United States Patent
Brydon et al.

(10) Patent No.: US 6,526,974 B1
(45) Date of Patent: *Mar. 4, 2003

(54) PRESSURE CONTROL IN CPAP TREATMENT OR ASSISTED RESPIRATION

(75) Inventors: John William Ernest Brydon, Waverton (AU); Peter John Deacon Wickham, Five Dock (AU); Miroslav Bachak, Wahroonga (AU); Shane Douglas Hollis, Denistone (AU)

(73) Assignee: ResMed Limited, North Ryde (AU)

(*) Notice: Subject to any disclaimer, the term of this patent is extended or adjusted under 35 U.S.C. 154(b) by 0 days.

This patent is subject to a terminal disclaimer.

(21) Appl. No.: 09/642,824

(22) Filed: Aug. 22, 2000

Related U.S. Application Data

(63) Continuation of application No. 08/894,305, filed as application No. PCT/AU98/00586 on Sep. 18, 1996, now Pat. No. 6,182,657.

(30) Foreign Application Priority Data

Sep. 18, 1995 (AU) .............................. PN5498
Dec. 28, 1995 (AU) .............................. PN7359

(51) Int. Cl.[7] ................................ A62B 9/02
(52) U.S. Cl. .................... 128/205.24; 128/204.18; 128/204.21; 128/204.23; 128/204.24; 137/625.18
(58) Field of Search .............. 128/204.18, 204.21, 128/204.23, 204.24, 205.24; 415/1, 10, 15, 17, 203, 206, 148, 159; 137/102, 625.18

(56) References Cited

U.S. PATENT DOCUMENTS

| | | |
|---|---|---|
| 2,664,961 A | 1/1954 | Goede |
| 2,904,033 A | 9/1959 | Shane |
| 3,099,985 A | 8/1963 | Wilson et al. |
| 3,502,100 A | 3/1970 | Jonson |
| 3,559,638 A | 2/1971 | Potter |
| 3,595,228 A | 7/1971 | Simon et al. |
| 3,611,801 A | 10/1971 | Paine et al. |
| 3,726,270 A | 4/1973 | Griffis et al. |
| 3,741,208 A | 6/1973 | Jonsson et al. |
| 3,783,893 A | 1/1974 | Davison |
| 3,802,417 A | 4/1974 | Lang |
| 3,817,246 A | 6/1974 | Weigl |

(List continued on next page.)

FOREIGN PATENT DOCUMENTS

| | | |
|---|---|---|
| AU | 62221/90 | 3/1991 |
| AU | 76019/91 | 1/1992 |

(List continued on next page.)

OTHER PUBLICATIONS

Derwent: Flowmeter for fluids–has turbine transducer and volumetric sensor for simultaneous calibration.

Mark Kantrowitz, Erik Horskotte and Cliff Joslyn; "Answers to Frequently Asked Questions about Fuzzy Logic and Fuzzy Expert Systems" Version 1.24 last Modified 20 2 96.

(List continued on next page.)

Primary Examiner—Aaron J. Lewis
Assistant Examiner—Joseph Weiss, Jr.
(74) Attorney, Agent, or Firm—Pillsbury Winthrop LLP

(57) ABSTRACT

The pressure of breathable gas exiting a flow generator is controlled by adjusting the efficiency of the flow generator. In one embodiment, a baffle plate of a control element can restrict the open entry area of a motor driven turbine of the flow generator. In another embodiment, the degree of opening of the mouth of the flow generator inlet is automatically adjustable in response to the needs of the user, hence creating a pneumatic impedance, and which simultaneously controls, in the same manner, the impedance of the outlet of the device.

4 Claims, 14 Drawing Sheets

U.S. PATENT DOCUMENTS

| | | |
|---|---|---|
| 3,882,847 A | 5/1975 | Jacobs |
| 3,903,875 A | 9/1975 | Hughes |
| 3,914,994 A | 10/1975 | Banner |
| 3,932,054 A | 1/1976 | McKelvey |
| 3,973,564 A | 8/1976 | Carden |
| 3,985,467 A | 10/1976 | Lefferson |
| 3,989,037 A | 11/1976 | Franetzki |
| 3,992,598 A | 11/1976 | Welsh et al. |
| 3,995,661 A | 12/1976 | Van Fossen |
| 4,006,634 A | 2/1977 | Billette et al. |
| 4,083,245 A | 4/1978 | Osborn |
| 4,109,749 A | 8/1978 | Sweet |
| 4,119,096 A | 10/1978 | Drews |
| 4,206,754 A | 6/1980 | Cox et al. |
| 4,226,234 A * | 10/1980 | Gunderson ............ 128/205.24 |
| 4,249,527 A | 2/1981 | Ko et al. |
| 4,265,591 A | 5/1981 | Gurbin |
| 4,279,250 A * | 7/1981 | Valenta et al. ......... 128/200.14 |
| 4,301,833 A | 11/1981 | Donald, III |
| 4,312,235 A | 1/1982 | Daigle |
| 4,320,766 A | 3/1982 | Alihanka et al. |
| 4,322,594 A | 3/1982 | Brisson |
| 4,381,788 A | 5/1983 | Douglas |
| 4,387,722 A | 6/1983 | Kearns |
| 4,396,034 A | 8/1983 | Cherniak |
| 4,405,290 A | 9/1983 | Rannenberg |
| 4,411,285 A * | 10/1983 | Oswell ....................... 137/112 |
| 4,414,982 A | 11/1983 | Durkan |
| 4,433,693 A | 2/1984 | Hochstein |
| 4,448,058 A | 5/1984 | Jaffe et al. |
| 4,449,525 A | 5/1984 | White et al. |
| 4,481,944 A | 11/1984 | Bunnell |
| 4,499,914 A | 2/1985 | Schebler |
| 4,506,666 A | 3/1985 | Durkan |
| 4,519,399 A | 5/1985 | Hori |
| 4,522,233 A * | 6/1985 | Mojadad ................. 137/625.47 |
| 4,530,334 A | 7/1985 | Pagdin |
| 4,550,615 A | 11/1985 | Grant |
| 4,550,726 A | 11/1985 | McEwen |
| 4,558,710 A | 12/1985 | Eichler |
| 4,570,631 A | 2/1986 | Durkan |
| 4,576,179 A | 3/1986 | Manus et al. |
| 4,579,114 A | 4/1986 | Gray et al. |
| 4,580,575 A | 4/1986 | Birnbaum et al. |
| 4,592,880 A | 6/1986 | Murakami |
| 4,595,016 A | 6/1986 | Fertig et al. |
| 4,602,644 A | 7/1986 | DiBenedetto et al. |
| 4,630,614 A | 12/1986 | Atlas |
| 4,637,386 A | 1/1987 | Baum |
| 4,648,396 A | 3/1987 | Raemer |
| 4,648,407 A | 3/1987 | Sackner |
| 4,655,213 A | 4/1987 | Rapoport et al. |
| 4,662,819 A | 5/1987 | Lakowske et al. |
| 4,677,975 A | 7/1987 | Edgar et al. |
| 4,686,974 A | 8/1987 | Sato et al. |
| 4,686,999 A | 8/1987 | Snyder et al. |
| 4,738,266 A | 4/1988 | Thatcher |
| 4,747,403 A | 5/1988 | Gluck et al. |
| 4,773,411 A | 9/1988 | Downs |
| 4,777,963 A | 10/1988 | McKenna |
| 4,784,130 A | 11/1988 | Kenyon et al. |
| 4,795,314 A | 1/1989 | Prybella et al. |
| 4,802,485 A | 2/1989 | Bowers et al. |
| 4,803,471 A | 2/1989 | Rowland |
| 4,819,629 A | 4/1989 | Jonson |
| 4,823,788 A | 4/1989 | Smith et al. |
| 4,825,802 A | 5/1989 | Le Bec |
| 4,827,922 A | 5/1989 | Champain et al. |
| 4,838,258 A | 6/1989 | Dryden et al. |
| 4,844,085 A | 7/1989 | Gattinoni |
| 4,856,506 A | 8/1989 | Jinotti |
| 4,860,766 A | 8/1989 | Sackner |
| 4,870,960 A | 10/1989 | Hradek |
| 4,870,963 A | 10/1989 | Carter |
| 4,887,607 A | 12/1989 | Beatty |
| 4,913,401 A | 4/1990 | Handke |
| 4,915,103 A | 4/1990 | Visveshwara et al. |
| 4,928,684 A | 5/1990 | Breitenfelder et al. |
| 4,938,210 A | 7/1990 | Shene |
| 4,938,212 A | 7/1990 | Snook et al. |
| 4,944,310 A | 7/1990 | Sullivan |
| 4,957,107 A | 9/1990 | Sipin |
| 4,960,118 A | 10/1990 | Pennock |
| 4,971,065 A | 11/1990 | Pearce |
| 4,972,842 A | 11/1990 | Korten et al. |
| 4,982,738 A | 1/1991 | Griebel |
| 4,986,269 A | 1/1991 | Hakkinen |
| 4,989,599 A | 2/1991 | Carter |
| 4,991,576 A | 2/1991 | Henkin et al. |
| 5,009,635 A | 4/1991 | Scarberry |
| 5,024,219 A | 6/1991 | Dietz |
| 5,046,491 A | 9/1991 | Derrick |
| 5,048,515 A | 9/1991 | Sanso |
| 5,052,400 A | 10/1991 | Dietz |
| 5,063,922 A | 11/1991 | Hakkinen |
| 5,063,938 A | 11/1991 | Beck et al. |
| 5,065,756 A | 11/1991 | Rapoport |
| 5,069,222 A | 12/1991 | McDonald, Jr. |
| 5,090,248 A | 2/1992 | Cimmino et al. |
| 5,099,837 A | 3/1992 | Russel, Sr. et al. |
| 5,105,354 A | 4/1992 | Nishimura |
| 5,107,830 A | 4/1992 | Younes |
| 5,107,831 A | 4/1992 | Halpern et al. |
| 5,117,819 A | 6/1992 | Servidio et al. |
| 5,129,390 A | 7/1992 | Chopin et al. |
| 5,134,995 A | 8/1992 | Gruenke et al. |
| 5,148,802 A | 9/1992 | Sanders et al. |
| 5,161,525 A | 11/1992 | Kimm et al. |
| 5,161,541 A | 11/1992 | Bowman et al. |
| 5,165,398 A | 11/1992 | Bird |
| 5,170,798 A | 12/1992 | Riker |
| 5,174,287 A | 12/1992 | Kallok et al. |
| 5,178,138 A | 1/1993 | Walstrom et al. |
| 5,183,983 A | 2/1993 | Knop |
| 5,186,166 A * | 2/1993 | Riggs et al. ............ 128/203.15 |
| 5,190,048 A | 3/1993 | Wilkinson |
| 5,195,528 A | 3/1993 | Hok |
| 5,199,424 A | 4/1993 | Sullilvan et al. |
| 5,203,343 A | 4/1993 | Axe et al. |
| 5,230,330 A | 7/1993 | Price |
| 5,231,979 A | 8/1993 | Rose et al. |
| 5,231,983 A | 8/1993 | Matson et al. |
| 5,233,983 A | 8/1993 | Markowitz |
| 5,239,994 A | 8/1993 | Atkins |
| 5,239,995 A | 8/1993 | Estes et al. |
| 5,245,995 A | 9/1993 | Sullivan et al. |
| 5,259,373 A | 11/1993 | Gruenke et al. |
| 5,271,391 A | 12/1993 | Graves |
| 5,280,784 A | 1/1994 | Kohler |
| 5,293,864 A | 3/1994 | McFadden |
| 5,295,491 A | 3/1994 | Gevins |
| 5,299,568 A * | 4/1994 | Forare et al. ........... 128/205.11 |
| 5,303,698 A | 4/1994 | Tobia et al. |
| 5,303,700 A | 4/1994 | Weismann et al. |
| 5,305,787 A | 4/1994 | Thygesen |
| 5,311,875 A | 5/1994 | Stasz |
| 5,313,937 A | 5/1994 | Zdrojkowski |
| 5,322,057 A | 6/1994 | Raabe et al. |
| 5,327,899 A | 7/1994 | Harris et al. |
| 5,335,654 A | 8/1994 | Rapoport |
| 5,335,656 A | 8/1994 | Bowe et al. |

| Patent Number | Date | Inventor(s) | Class |
|---|---|---|---|
| 5,343,878 A | 9/1994 | Scarberry et al. | |
| 5,353,788 A | 10/1994 | Miles | |
| 5,355,872 A * | 10/1994 | Riggs et al. | 128/200.21 |
| 5,360,008 A | 11/1994 | Campbell, Jr. | |
| 5,373,842 A | 12/1994 | Olsson et al. | |
| 5,383,449 A * | 1/1995 | Forare et al. | 128/205.11 |
| 5,388,571 A | 2/1995 | Roberts et al. | |
| 5,394,882 A | 3/1995 | Mawhinney | |
| 5,398,673 A | 3/1995 | Lambert | |
| 5,400,777 A | 3/1995 | Olsson et al. | |
| 5,404,871 A | 4/1995 | Goodman et al. | |
| 5,413,111 A | 5/1995 | Wilkinson | |
| 5,433,193 A | 7/1995 | Sanders et al. | |
| 5,438,980 A | 8/1995 | Phillips | |
| 5,443,061 A | 8/1995 | Champain et al. | |
| 5,443,075 A | 8/1995 | Holscher | |
| 5,448,996 A | 9/1995 | Bellin et al. | |
| 5,458,137 A | 10/1995 | Axe et al. | |
| 5,479,920 A | 1/1996 | Piper et al. | |
| 5,479,939 A | 1/1996 | Ogino | |
| 5,483,969 A | 1/1996 | Testerman et al. | |
| 5,490,502 A | 2/1996 | Rapoport et al. | |
| 5,492,113 A | 2/1996 | Estes et al. | |
| 5,503,146 A | 4/1996 | Froehlich et al. | |
| 5,507,282 A | 4/1996 | Younes | |
| 5,509,404 A | 4/1996 | Lloyd et al. | |
| 5,509,414 A | 4/1996 | Hok | |
| 5,513,631 A | 5/1996 | McWilliams | |
| 5,517,983 A | 5/1996 | Deighan et al. | |
| 5,522,382 A | 6/1996 | Sullivan et al. | |
| 5,526,805 A | 6/1996 | Lutz et al. | |
| RE35,295 E | 7/1996 | Estes et al. | |
| 5,535,738 A | 7/1996 | Estes et al. | |
| 5,535,739 A | 7/1996 | Rapoport et al. | |
| 5,537,997 A | 7/1996 | Mechlenburg et al. | |
| 5,540,219 A | 7/1996 | Mechlenburg et al. | |
| 5,540,220 A | 7/1996 | Gropper | |
| 5,540,733 A | 7/1996 | Testerman et al. | |
| 5,546,933 A | 8/1996 | Rapoport et al. | |
| 5,546,952 A | 8/1996 | Erickson | |
| 5,549,106 A | 8/1996 | Gruenke et al. | |
| 5,549,655 A | 8/1996 | Erickson | |
| 5,551,418 A | 9/1996 | Estes et al. | |
| 5,551,419 A | 9/1996 | Froelich et al. | |
| 5,558,099 A | 9/1996 | Bowman et al. | |
| RE35,339 E | 10/1996 | Rapoport | |
| 5,567,127 A | 10/1996 | Wentz | |
| 5,570,682 A | 11/1996 | Johnson | |
| 5,588,439 A | 12/1996 | Hollub | |
| 5,598,838 A | 2/1997 | Servidio et al. | |
| 5,605,151 A | 2/1997 | Lynn | |
| 5,608,647 A | 3/1997 | Rubsamen et al. | |
| 5,617,846 A | 4/1997 | Graetz et al. | |
| 5,630,411 A | 5/1997 | Holscher | |
| 5,632,269 A | 5/1997 | Zdrojkowski | |
| 5,633,552 A | 5/1997 | Lee et al. | |
| 5,642,730 A | 7/1997 | Baran | |
| 5,645,053 A | 7/1997 | Remmers et al. | |
| 5,645,054 A | 7/1997 | Cotner et al. | |
| 5,647,351 A | 7/1997 | Wesimann et al. | |
| 5,655,520 A | 8/1997 | Howe et al. | |
| 5,655,522 A | 8/1997 | Mechlenburg et al. | |
| 5,660,171 A | 8/1997 | Kimm et al. | |
| 5,666,946 A | 9/1997 | Langenback | |
| 5,682,878 A | 11/1997 | Ogden | |
| 5,685,296 A | 11/1997 | Zdrojkowski et al. | |
| 5,687,912 A * | 11/1997 | Denyer | 239/343 |
| 5,694,926 A | 12/1997 | DeVries et al. | |
| 5,701,883 A | 12/1997 | Hete et al. | |
| 5,704,345 A | 1/1998 | Berthon-Jones | |
| 5,715,812 A | 2/1998 | Deighan et al. | |
| 5,730,121 A | 3/1998 | Hawkins | |
| 5,740,795 A | 4/1998 | Brydon | |
| 5,794,614 A | 8/1998 | Gruenke et al. | |
| 5,794,615 A | 8/1998 | Estes | |
| 5,797,852 A | 8/1998 | Karakasoglu et al. | |
| 5,803,066 A | 9/1998 | Rapoport et al. | |
| 5,813,401 A * | 9/1998 | Radcliff et al. | 128/205.24 |
| 5,823,179 A * | 10/1998 | Grychowski et al. | 128/200.18 |
| 5,823,187 A | 10/1998 | Estes et al. | |
| 5,845,636 A | 12/1998 | Gruenke et al. | |
| 5,850,835 A * | 12/1998 | Takaki et al. | 128/204.18 |
| 5,931,163 A * | 8/1999 | Stegmann et al. | 128/204.26 |
| 5,979,443 A | 11/1999 | Dingley | |
| 6,182,657 B1 * | 2/2001 | Brydon et al. | 128/205.24 |
| 6,253,764 B1 * | 7/2001 | Calluaud | 128/204.18 |
| 6,269,839 B1 * | 8/2001 | Wickham et al. | 137/625.65 |

FOREIGN PATENT DOCUMENTS

| | | | |
|---|---|---|---|
| AU | | 33877/93 | 4/1993 |
| AU | | 59270/90 | 5/1993 |
| AU | | 38508/93 | 7/1993 |
| AU | | 48748/93 | 9/1993 |
| AU | | 52628/93 | 7/1994 |
| AU | | 79174/94 | 6/1995 |
| AU | | 34471/95 | 2/1996 |
| AU | | 40711-95 | 4/1996 |
| AU | | 34353 | 5/1996 |
| AU | | 39130/95 | 6/1996 |
| DE | | 459104 | 4/1928 |
| DE | | 3015279 A1 | 10/1981 |
| DE | | 3429345 A1 | 12/1983 |
| DE | | 3345067 A1 | 6/1984 |
| DE | | 34 02 603 A1 | 8/1985 |
| DE | | 3537507 A1 | 4/1987 |
| DE | | 3539073 A1 | 5/1987 |
| DE | WO 94/16759 | | 8/1994 |
| DE | | 4432219 C1 | 4/1996 |
| DE | | 296 12 119 U1 | 12/1996 |
| DE | | 195 36 632 A1 | 3/1997 |
| EP | | 0 062 166 A2 | 10/1982 |
| EP | | 0 066 451 A1 | 12/1982 |
| EP | | 0 665 451 A1 | 12/1982 |
| EP | | 0 088 761 | 9/1983 |
| EP | | 0 164 500 A2 | 3/1985 |
| EP | | 164-500 A | 3/1985 |
| EP | | 164500 | 12/1985 |
| EP | | 0 171 321 A1 | 2/1986 |
| EP | | 0 185 980 | 7/1986 |
| EP | | 0 236 850 A2 | 9/1987 |
| EP | | 0 872 643 A2 | 3/1988 |
| EP | | 0 283 141 | 9/1988 |
| EP | | 298 367 A2 | 1/1989 |
| EP | | 0 425 092 A1 | 9/1989 |
| EP | | 0 452 001 A2 | 3/1990 |
| EP | | 0 388 525 A1 | 9/1990 |
| EP | | 425092 | 5/1991 |
| EP | | 0 461 281 A1 | 12/1991 |
| EP | | 481 459 A1 | 4/1992 |
| EP | | 0 481 459 A1 | 4/1992 |
| EP | | 0514 744 | 11/1992 |
| EP | | 0 548 624 | 6/1993 |
| EP | | 0549299 A2 | 6/1993 |
| EP | | 606 687 A2 | 7/1994 |
| EP | | 0705615 A1 | 9/1994 |
| EP | | 0651971 A1 | 5/1995 |
| EP | | 0 661 071 A1 | 7/1995 |
| EP | | 0 656 216 A2 | 9/1995 |
| EP | | 178 925 A2 | 4/1996 |
| EP | | 0 709 107 A1 | 5/1996 |
| EP | | 0 714 670 A2 | 6/1996 |
| EP | | 0 765 631 A2 | 4/1997 |

| | | |
|---|---|---|
| EP | 0 788 805 A2 | 8/1997 |
| EP | 0 839 545 A1 | 5/1998 |
| FR | 2 574 657 A1 | 6/1986 |
| FR | 2 672 221 A1 | 8/1992 |
| FR | 2682042 A1 | 4/1993 |
| FR | 1255865 | 12/1996 |
| GB | 1432572 | 4/1976 |
| GB | 1 444 053 | 7/1976 |
| GB | 1583273 | 1/1981 |
| GB | 2054387 | 2/1981 |
| GB | 2 077 444 A | 12/1981 |
| GB | 2 147 506 A | 5/1985 |
| GB | 2 164 569 A | 3/1986 |
| GB | 2 166 871 A | 5/1986 |
| GB | 2 205 167 A | 11/1988 |
| GB | 2 221 302 A | 1/1990 |
| GB | 2 254 700 A | 10/1992 |
| GB | 2 261 290 A | 5/1993 |
| GB | 2 271 811 A | 4/1994 |
| GB | 2 294 400 A | 5/1996 |
| JP | 54-104369 | 8/1979 |
| JP | 60-212607 | 10/1985 |
| JP | 62-103297 | 4/1987 |
| JP | 63-275352 | 11/1988 |
| JP | 2-173397 | 12/1988 |
| JP | 4-70516 A | 3/1992 |
| JP | 06249741 A | 9/1994 |
| JP | 6-249742 A | 9/1994 |
| JP | 07280609 A | 10/1995 |
| JP | 8019610 A | 1/1996 |
| SE | 1710064 A1 | 2/1992 |
| SE | 467041 B | 5/1992 |
| WO | WO 80/01044 | 5/1980 |
| WO | WO 82/03326 | 10/1982 |
| WO | WO 86/05965 | 10/1986 |
| WO | WO 86/06969 | 12/1986 |
| WO | WO 87/02577 | 5/1987 |
| WO | WO 89/09565 | 10/1988 |
| WO | WO 88/10108 | 12/1988 |
| WO | WO 90/09146 | 8/1990 |
| WO | WO 90/14121 | 11/1990 |
| WO | WO 91/12051 | 8/1991 |
| WO | WO 91/19456 | 12/1991 |
| WO | WO 92/11054 | 7/1992 |
| WO | WO 92/15353 | 9/1992 |
| WO | WO 82/03548 | 10/1992 |
| WO | WO 92/18201 | 10/1992 |
| WO | WO 92/22244 | 12/1992 |
| WO | WO 93/08857 | 5/1993 |
| WO | WO 93/09834 | 5/1993 |
| WO | WO 93/21982 | 11/1993 |
| WO | WO 93/24169 | 12/1993 |
| WO | WO 94/04071 | 3/1994 |
| WO | WO 94/20018 | 9/1994 |
| WO | WO 94/20051 | 9/1994 |
| WO | WO 94/23780 | 10/1994 |
| WO | WO 95/32016 | 11/1995 |
| WO | WO 95/34917 | 12/1995 |
| WO | 96/04043 | 2/1996 |
| WO | WO 96/16688 | 6/1996 |
| WO | WO 96/32055 | 10/1996 |
| WO | WO 96/36279 | 11/1996 |
| WO | WO 96/40337 | 12/1996 |
| WO | WO 96/41571 | 12/1996 |
| WO | WO 96/41651 | 12/1996 |
| WO | WO 97/02064 | 1/1997 |
| WO | WO 97/05824 | 2/1997 |
| WO | WO 97/10019 | 3/1997 |
| WO | WO 97/10868 | 3/1997 |
| WO | WO 97/14354 | 4/1997 |
| WO | WO 97/15343 | 5/1997 |
| WO | WO 97/18752 | 5/1997 |
| WO | WO 97/20499 | 6/1997 |
| WO | WO 97/22377 | 6/1997 |
| WO | WO 97/28838 | 8/1997 |
| WO | WO 97/41812 | 11/1997 |
| WO | WO 98/06449 | 2/1998 |
| WO | WO 98/25662 | 6/1998 |
| WO | WO 98/33433 | 8/1998 |
| WO | WO 98/35715 | 8/1998 |
| WO | WO 98/36245 | 8/1998 |
| WO | WO 98/36338 | 8/1998 |
| WO | WO 98/47554 | 10/1998 |
| WO | WO 98/52467 | 11/1998 |
| WO | WO 98/57691 | 12/1998 |

OTHER PUBLICATIONS

New! Breas PV 100 CPAP First Class Quality and Function. At the right Price; Jul. 4, 1998, pp 1–2.
PV 101 Bi Level CPAP and PV 102 Bi–Level Time; pp 1–3.
Prodigy Medical Supplies Co. Ltd.; CPAP.
Puritan Bennett; Companion 318 Nasal CPAP System; 5/93.
Nellcor Puritan Bennett; Announcing the Goodnight 314 and GoodKnight 318 Nasal CPAP Systems.
Puritan Bennett; Clean, Quiet, and Comfortable . . . The Companion's 515 Nasal CPAP System; 6/88.
DeVilbiss Night Guard Nasal CPAP for the Treatment of Obstructive Sleep Apnea.
Sunrise; DeVilbiss Horizon LT 8001 Nasal CPAP Therapy Small in Size, big features.
Devilbiss; Revitalizer Soft Start; The Facts Speak for Themselves.
Tranquility; Performance CPAP Advantage.
Healthdyne International; Tranquility Plus.
Respironics Inc.; Respironics' Solo CPAP System Provides Simplified OSA Therapy at an Outstanding value; Sep. 19, 1996.
Respironics Inc.; The First Family of OSA Therapy; 1991.
Fisher & Paykel Healthcare; HC200 Series Nasal CPAP Blower & Heated Humidifier.
Pierre Medical; Morphee Plus appareil de traitment des apnees du sommeil manuel d'utilisation.
Weinmann:Hamburg; Somnotron nCPAP–Great WM 2300.
Puritan Bennett; 515a Part of Our Blueprint for the Future; 03/90.
Puritan Bennett; Companion 320 I/E Bi–Level Respiratory System; 4/93.
ResMed; Sullivan VPAP II & II ST.
ResMed; The Sullivan V Family of CPAP Systems.
ResMed; The AutoSet Portable II.
ResMed; Sullivan Nasal CPAP System.
ResMed; The Sullivan IIID.
ResMed; The Sullivan Comfort.
DeVilbiss a Division of Sunrise Medical; Expand your Horizons With The Horizons.
Healthdyne Technologies; Home Health Care Dealer; The Journal of Home Medical Equipment and Services/Supplier; Nov. and Dec. 1997.
Healthdyne International; Tranquility Quest, The Compact CPAP for Greater patient comfort.
AirStep; Medical Products . . . Stand the Test of Time.
MAP Medical Progress for Physician und Patient; The Gentle Therapy for Sleep–Related Breathing Disorders.
Taema; Ventilation CP 90.
DPAP; Breath, by breath, by breath.
Lifecare; Smallest. Quietest. Smartest.

Lifecare; Quiet CPAP System for Maximum Compliance; 1991.
Lifecare; Software Nasal Mask, Custom Nasal Masks; 1991.
Nidek Medical; Silenzio.
Weinmann; Just to Fell Well, Sensitive Sleep Apnoea Therapy with Somnotron 3 and Somno–Mask System.
Respironics Inc.; Aria CPAP System.
Respironics Inc.; SleepEasy III A New Dawn in Patient Compliance.
Respironics Inc.; Muliple Choice REMstar Choice Nasal CPAP System.
Maxll nCPAP and Moritz II Bi–Level Brochure.
Fluid Mechanics, $4^{th}$ ed., pp. 279–285, 1996, Prentice Hall Inc., Granet, Irving.
The International Dictionary of Physics & Electronics, $2^{nd}$ Ed., p. 379, 1961, D. Van Nostrand Co., Inc.

* cited by examiner

PRESSURE CONTROL IN CPAP TREATMENT OR ASSISTED RESPIRATION

This is a continuation of Application No. 08/894,305, filed Apr. 20, 1998, now issued as U.S. Pat. No. 6,182,657, which is a 371 of PCT/AU 96/00586 filed Sep. 18, 1996 the entirety of which is hereby incorporated by reference herein.

FIELD OF THE INVENTION

This invention relates to apparatus and methods for the control of pressure in the administration of continuous positive airway pressure (CPAP) treatment or assisted respiration.

BACKGROUND OF THE INVENTION

The administration of CPAP is common in the treatment of Obstructive Sleep Apnea (OSA) syndrome and Upper Airway Resistance syndrome. It has been postulated that CPAP treatment effectively acts as a pneumatic splint of a patient's upper airway by providing air or breathable gas at a pressure elevated above atmospheric pressure to the entrance of the patient's airway. Treatment pressures in the range 4–25 cm $H_2O$ are commonly encountered.

Common to all forms of CPAP apparatus is a mask worn by a patient having connection via a flexible air delivery tube to a flow generator. Most often, the flow generator is driven by an electric motor that is under the control of a motor controller. In this specification reference to a "mask" is to be understood as including a nose mask, a mouth mask. a nose and mouth mask in combination, nasal prongs or nasal pillows, or a full face mask.

CPAP treatment can be in a number of forms, including (i) the maintenance of a constant treatment pressure level, (ii) alternating between two constant levels in synchronism with the inspiratory and expiratory phases of respiration ("bi-level CPAP"), and (iii) having an autosetting level in accordance with a patient's therapeutic needs. In all of these cases there must be control over the pressure of air or breathable gas supplied to the patient's airway.

In one form in the prior art, control over the treatment pressure is achieved by speed control of the electric motor driving the turbine (or fan) that together constitute the flow generator. In the case of bi-level CPAP, the motor must be able to accelerate (or decelerate) respectively to double (or half) its operational speed within about 100 ms. For typical CPAP treatment, this equates to the need to supply (or sink) approximately twice the steady state electrical power within the noted time interval. Disadvantages in motor performance associated with the rapid transitions in speed are, for example, noise due to magnetostrictive effects and bearing vibration, and increased thermal dissipation requirements. Lower noise will increase patient compliance with the treatment.

FIG. 1 shows, as a cross-sectional view, a conventional flow generator 10 comprising a chamber 12 that is segregated from the casing 14 of the CPAP apparatus. The casing 14 houses the control circuitry (not shown) associated with the flow generator 10. The flow generator further is comprised by a motor 16 driving an induced flow centrifugal turbine (impeller) 18, which induces the flow of air or breathable gas by an air inlet 20 to pass the air or breathable gas under pressure by an air outlet 22 to the air delivery tube (not shown) and so to the mask (also not shown). The turbine 18 has radially directed impeller blades 24. The alternate use of axial fans is known also in CPAP apparatus.

Another form of controllable flow generator involves operation of the driving motor at a constant speed, and venting or bleeding-off excess air from the output side of the turbine. As shown in FIG. 2, the turbine 18 is connected to a plenum chamber 30 by a supply pipe 32. The plenum chamber has a controllable spill valve 34 operable to indexingly open and close an opening 36 in the chamber wall to allow the venting of air to atmosphere so as to achieve the desired output pressure at the air outlet 38.

Such an arrangement also has disadvantages. Firstly there is excessive noise due to the venting of air when the treatment pressure is adjusted. This is particularly the case for each expiratory event during bi-level CPAP treatment when the treatment pressure typically is reduced from 16 cm $H_2O$ to 6 cm $H_2O$, and thus over one half of the pressure head of the air within the plenum chamber 30 must be vented by the spill valve 34. It is also difficult to maintain precise treatment pressure regulation, since small variations of the spill valve position give relatively large variations in the pressure at the air outlet 38. This configuration also leads to an inherently low maximum flow rate which can compromise the efficacy of CPAP treatment. In particular, the spill valve 34 works by increasing outlet flow from the plenum chamber 30, thereby increasing the pressure drop in the supply pipe 32 and the turbine 18, thus dropping the pressure in the plenum chamber. The combined pneumatic impedance of the supply pipe 32 and the turbine 18 limit the maximum achievable flow rate into the plenum chamber 30, and so to the patient, on subsequent closure of the spill valve 34.

An example of another prior art arrangement that operates on the output of the flow generator can be obtained from International Publication No. WO 90/14121 (PCT/US90/02800), in the name Puritan-Bennett Corp.

As is noted, the invention also has application to apparatus for the provision of assisted respiration. Use of the term "assisted respiration" is to be understood as embracing both ventilators and respirators. Ventilators can broadly be characterised as providing for patient ventilation in a volume cycled mode, and do the work of breathing for the patient. Respirators, on the other hand, may or may not do the complete work of breathing for a patient, and are characterised by their bi-level operation, with a large treatment pressure differential between inspiration and expiration and a high inspiratory treatment pressure, which may reach 30–40 cm $H_2O$.

DISCLOSURE OF THE INVENTION

It is an objective of the present invention to overcome or at least ameliorate one or more of the problems associated in the prior art. The gist of the invention is to provide control of output pressure by controlling the efficiency of a flow generator or its component turbine.

Therefore, the invention broadly discloses a controllable flow generator for the supply of breathable gas in the administration of CPAP treatment or assisted respiration, the flow generator comprising: a motor coupled to drive a turbine, an inlet for breathable gas in communication with the turbine, an outlet for the supply of said breathable gas at a pressure elevated above atmospheric pressure, and means to control the efficiency of the flow generator and thus the pressure of breathable gas exiting the flow generator.

In this specification the term "efficiency" in relation to a flow generator or to the component turbine is to be understood as the ability to pressurize a mass of air at a given flow rate and a given pressure.

In one preferred form the control means controls the efficiency of the turbine, and most preferably comprises adjustable pitch turbine blades or turbine louvres. In another preferred form, the control means controls the breathable gas available to the turbine. Alternatively, it controls the gas available to the inlet. Further, the control means can control the impedance of the outlet. The flow generator can further comprise pressure sensor means for sensing the pressure of air or breathable gas exiting the flow generator by the outlet, said sensed pressure being provided to said control means, and said control means further operable to compare said sensed pressure with a set pressure to maintain said exiting pressure substantially the same as said set pressure by controlling the efficiency of the turbine in accordance with the result of said comparison.

The invention further discloses a controllable flow generator for the supply of pressurised breathable gas in the administration of CPAP treatment or assisted respiration, the flow generator comprising a motor coupled to drive a turbine, an inlet for breathable gas in communication with the turbine. an outlet for the supply of said breathable gas at a pressure elevated above atmospheric pressure, and control means for controlling the breathable gas available to the turbine and thus the pressure of breathable gas at the outlet.

Advantageously, the control means acts to restrict the flow generator inlet. The restriction can be over a range of inlet opening. The range can be between the inlet fully open and partly or fully closed. For an operational rotational speed of said turbine, the limits of the range relative to inlet when open and at least partly closed respectively correspond to the highest outlet pressure and the lowest outlet pressure of supplied air or breathable gas.

In a preferred form, the control means can comprise means for closing at least a portion of a mouth of said inlet. Alternatively, said control means can comprise a controllable vane for at least partly restricting said inlet.

Alternatively, the control means acts to adjust the effective entry area of the turbine impeller open to the inlet. The adjustment can be over a range. The range can be between the total effective entry area of the turbine open to the inlet and partial or zero effective entry area of the turbine open to the inlet. For an operational rotational speed of said turbine, the limits of the range relative to said total effective surface area and at last partial effective entry area respectively correspond to the highest outlet pressure and the lowest outlet pressure of supplied air or breathable gas.

In a preferred form, the control means can comprise a positionally adjustable baffle that can block-off at least a portion of the effective mouth area open to the inlet.

In one particular preferred form, the control means acts, to cause the repeating sequential supply of breathable gas at said outlet at a first higher pressure and a second lower pressure. The flow generator can further comprise pressure sensor means for sensing pressure at said outlet, said sensed pressure provided to said control means, and said control means further operable to compare said sensed pressure with a set pressure to maintain said outlet pressure substantially the same as said set pressure by control of the breathable gas available to the turbine in accordance with the result of said comparison.

The invention further discloses CPAP treatment apparatus comprising a patient mask, an air delivery tube connected at one end to the mask, a flow generator connected to the other end of the air delivery tube and comprising a motor coupled to drive a turbine at an operational rotational speed. an inlet to receive breathable gas, an outlet for the supply of said breathable gas to said air delivery tube at a pressure elevated above atmospheric pressure, and control means for controlling the breathable gas available to the turbine and thus the pressure of breathable gas at said outlet.

In one preferred form the control means acts to restrict the flow generator inlet. Alternatively, the control means acts to adjust the effective area of the turbine open to the inlet.

The apparatus can further comprise a path for patient exhalation from said outlet by-passing the turbine. The exhalation path can vent to atmosphere or recirculate to said inlet.

Advantageously, the CPAP apparatus can be for the administration of bi-level CPAP treatment, and the control means is operable between two states respectively corresponding to a desired patient inspiratory treatment pressure, and the reduced desired patient expiratory treatment pressure.

Advantageously, the CPAP apparatus can be for the administration of a treatment pressure adjusting in accordance with patient need, wherein the control means has a continually adjusting current set level corresponding to the desired treatment pressure, and causes the outlet level to be controlled to maintain the pressure at the desired level.

The CPAP apparatus can further comprise pressure sensor means for sensing pressure at said outlet or at a point in said air delivery tube or in said mask, said sensed pressure provided to said control means, and said control means further operable to compare said sensed pressure with a current set pressure to maintain the treatment pressure substantially constant at the desired level in accordance with the result of the comparison.

In another preferred form, the CPAP treatment apparatus can be operable to maintain the treatment pressure at said mask substantially constant by continuous control of said control means.

The invention yet further discloses a method for control of the pressure of breathable gas delivered by a flow generator in the administration of CPAP treatment or assisted respiration, said method comprising the steps of operating said flow generator at an operational rotational speed whereby said breathable gas enters the turbine by an inlet of the flow generator and exits the turbine at a pressure elevated above atmospheric pressure, and controlling the breathable gas available to the turbine and thus the exit pressure.

All the above arrangements limit the through-put of breathable gas through the flow generator, compared with prior art arrangements which provide for pressure control by spilling excess gas, thereby resulting in concomitant increase in acoustic emissions and motor power requirements. Embodiments of the invention as defined can provide a controllable flow generator or CPAP apparatus that provides one or more of the advantages of lower power, lower acoustic noise, higher maximum air flow and improved pressure control in comparison with prior art arrangements. In one or more embodiments, the power supply for the flow generator can halve its rating, thus reducing cost, heat dissipation and occupied volume.

It will be understood that all references to "treatment pressure" include a continuous pressure that can vary with time if desired in accordance with treatment needs, and therefore is not necessarily of a constant level.

BRIEF DESCRIPTION OF THE DRAWINGS

A number of embodiments of the invention now will be described with reference to the accompanying drawings, in which.

DESCRIPTION OF PREFERRED EMBODIMENTS AND BEST MODE

Figure 1:
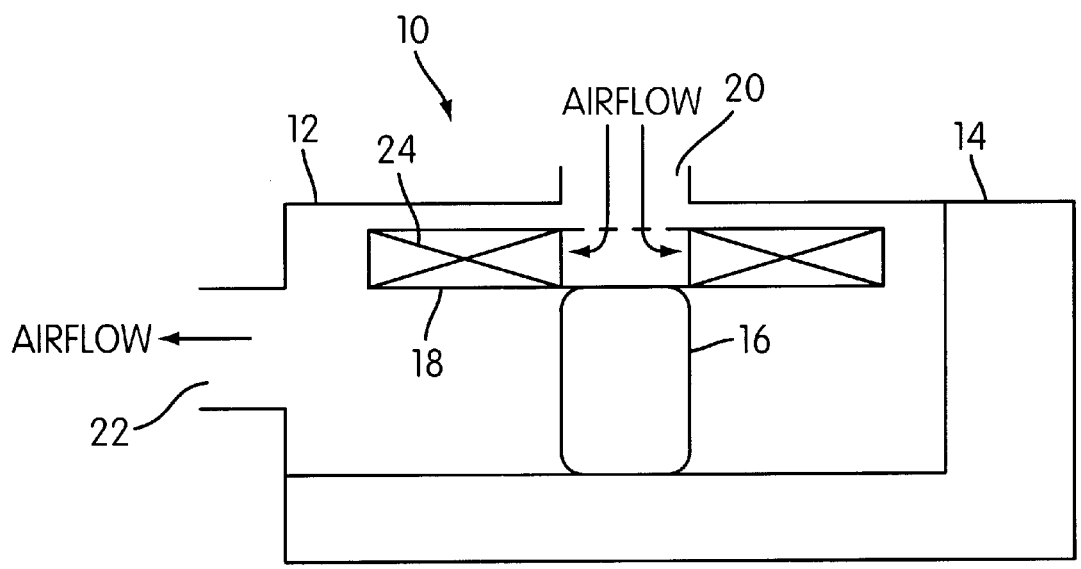
FIGS. 1 and 2 show examples of controllable flow generators in the prior art.
Figure 2:
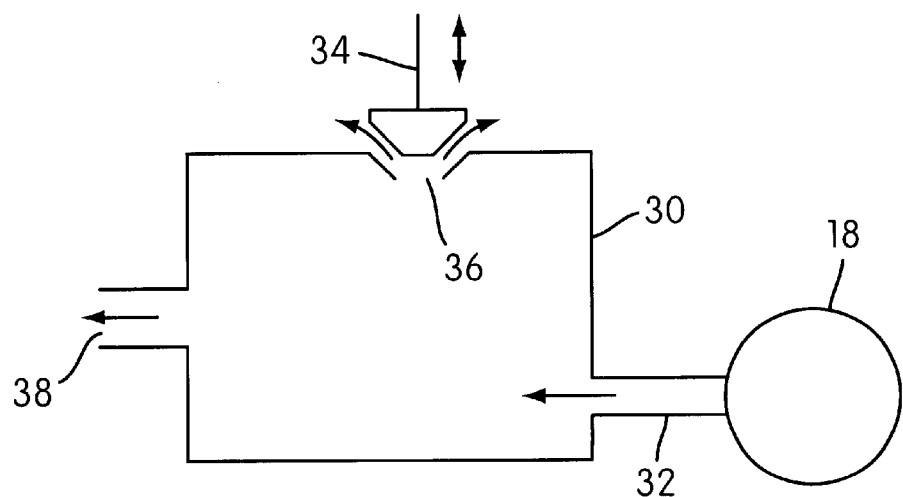

A number of controllable flow generator arrangements will be described, and it is to be understood that each and every arrangement can readily be incorporated into the CPAP apparatus manufactured by the present applicant, including the applicant's Sullivan™ III, Sullivan™ V, VPAP™ and Autoset™ Machines.

While the embodiments to be described refer to CPAP treatment, it is to be understood the invention equally is applicable to apparatus for assisted respiration treatment.

Where appropriate, the same reference numerals have been used to indicate a component part in common with other embodiments, or with the prior art.

Figure 3:
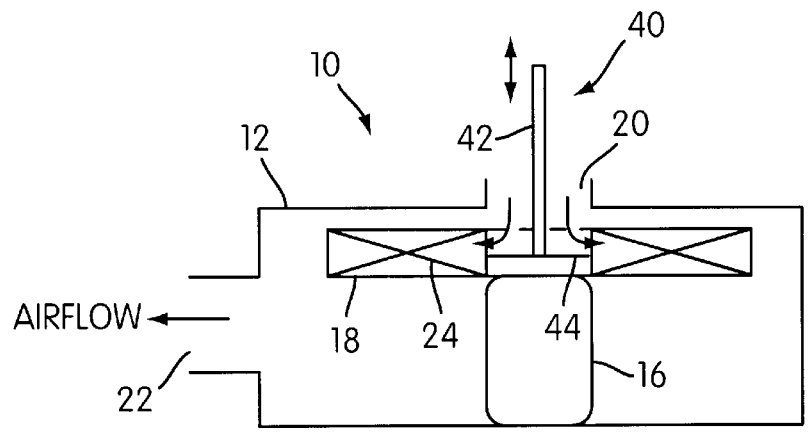
FIGS. 3–5 show a first embodiment of a controlled flow generator in accordance with the present invention.
Figure 4:
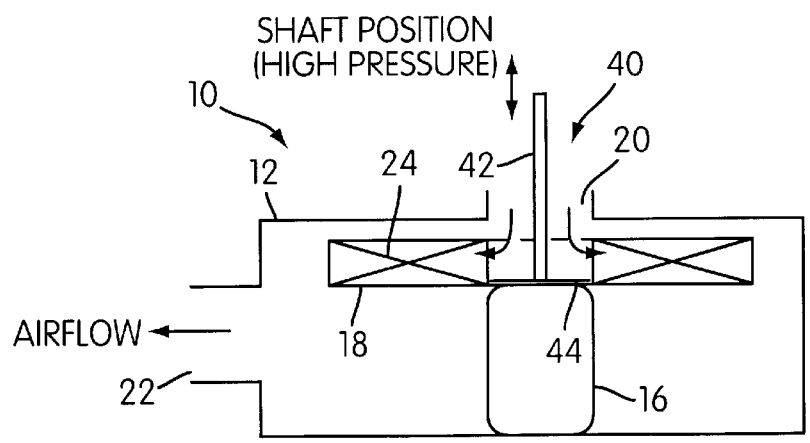
Figure 5:
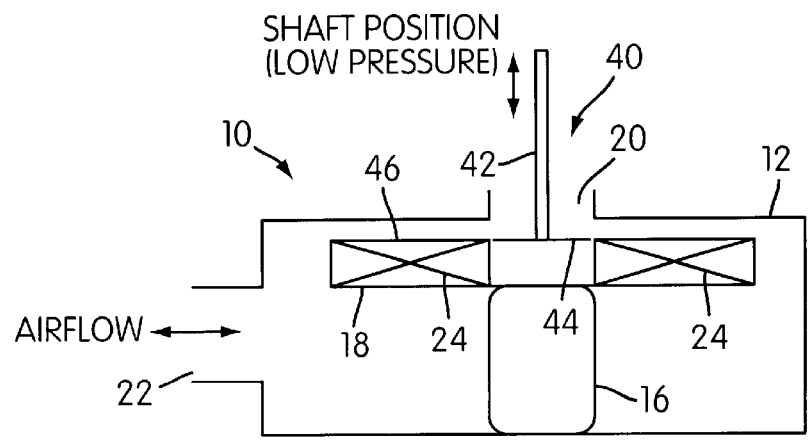

The embodiment shown in FIGS. 3 to 5 differs from the prior art arrangement shown in FIG. 1, in that a control element 40 is located in the air inlet path of the inlet 20 proximate the turbine impeller blades 24, and is comprised of a shaft 42 ending in a baffle plate 44. The control element 40 is caused to move vertically within a defined range by any convenient actuator (not shown) to change the effective entry area of the turbine impeller blades 24 open to the inlet 20. Generally, this controls the air or breathable gas available to the turbine 18, and more generally the efficiency of the flow generator. The baffle plate 44 may have a small clearance between its ends and the blades 24 (or blade housing) of the turbine 18. Equally, the baffle plate 44 could be in contact with the turbine 18 to rotate together with the turbine 18.

In operation of the flow generator 10, the motor 16 causes the turbine 18 to rotate at a near constant operational speed concomitant with, or slightly higher than, the maximum required treatment pressure to appear at the patient mask. In FIG. 4, the baffle plate 44 is located at its lower-most extent, thereby not restricting the flow of air from the inlet 20 to the turbine impeller blades 24. This represents the maximum pressure at the outlet 22, typically 20–30 cm $H_2O$ for CPAP treatment.

FIG. 5 shows the situation where the baffle plate 44 is arranged to be at its top-most extent of the range, whereby the air or breathable gas available to the turbine impeller blades is almost zero, in that the effective surface area of the blades 24 open to the inlet 20 is practically zero. Again, the motor 16 is driving the turbine 18 at the same operational rotational speed, in which case a near zero positive pressure (or at least a very low positive pressure) occurs at the outlet 22. In practice, this arrangement would represent a positive pressure at the outlet 22 of approximately 0–2 cm $H_2O$. A seal also may be provided at the top of the fan to ensure complete baffling by cooperation of the seal with the baffle plate 44 to avoid leaks around the edge of the baffle plate.

Thus by control of the control element 40, the flow generator's efficiency can be controlled, and different flow generator outlet (and therefore mask) treatment pressures can be obtained. As will be apparent, two pressures can be appropriately selected for implementation of bi-level CPAP by control of the baffle element 40. The higher inspiratory pressure corresponds with a lower position for the control element 40, while the lower expiratory pressure corresponds with a higher position of the control element 40.

The actuation devices coupled to the control element 40 have connection with breathing detection circuitry that detects transitions between patient inspiration and expiration, so that control over the movement of the baffle element 40 can be in synchronism with the patient's respiration phases. The present applicant's VPAP™ apparatus has such breathing detection circuitry.

Importantly, and as noted in FIG. 5, on patient expiration, a low impedance exhalation path 46 is provided, otherwise the benefit of a reduced treatment pressure during expiration may be negated by the patient being required to do excessive work during expiration. The expiration path 46 occurs between the outlet 22 and the inlet 20 by means of the open space around the sides and top of the turbine 18, creating a ready path to atmosphere. Without the expiration path a back pressure would be formed on patient expiration that would restrict the lowest treatment pressure achievable, that being particularly important to expiration treatment pressure in bi-level CPAP where an expiration treatment pressure of 4 cm $H_2O$ is not uncommon. Ideally, the back pressure on expiration should be limited to 2 cm $H_2O$ through the provision of the exhalation path 46. A low impedance exhalation path is preferred not only for bi-level CPAP treatment, but also for single level CPAP where, although the pressure remains constant, there should not be undue impedance to opposed flow due to patient expiration.

Figure 6:
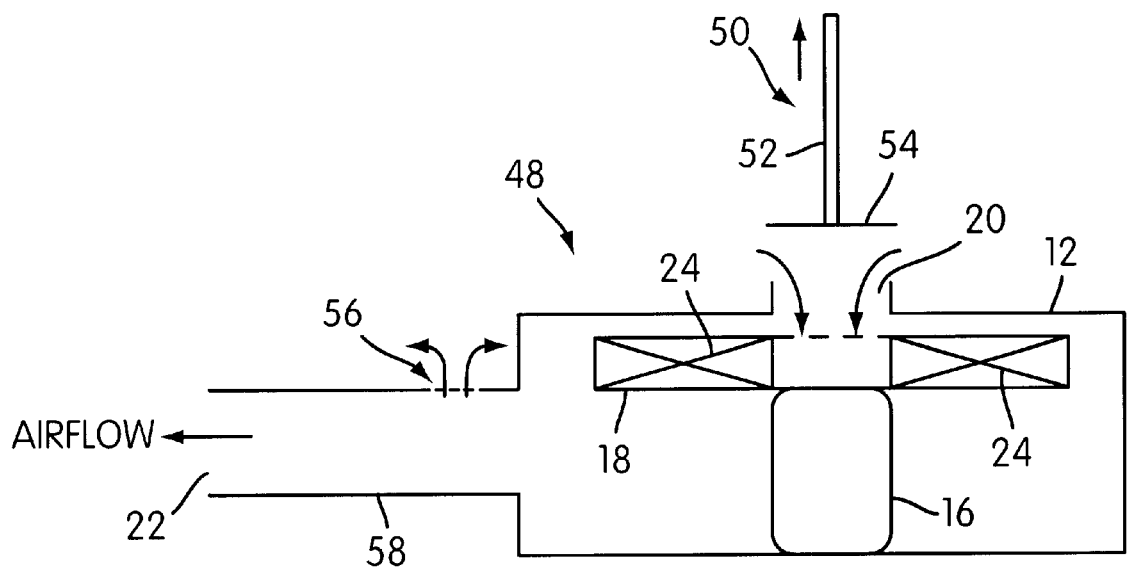
FIGS. 6 and 7 show another embodiment of a controlled flow generator.
Figure 7:
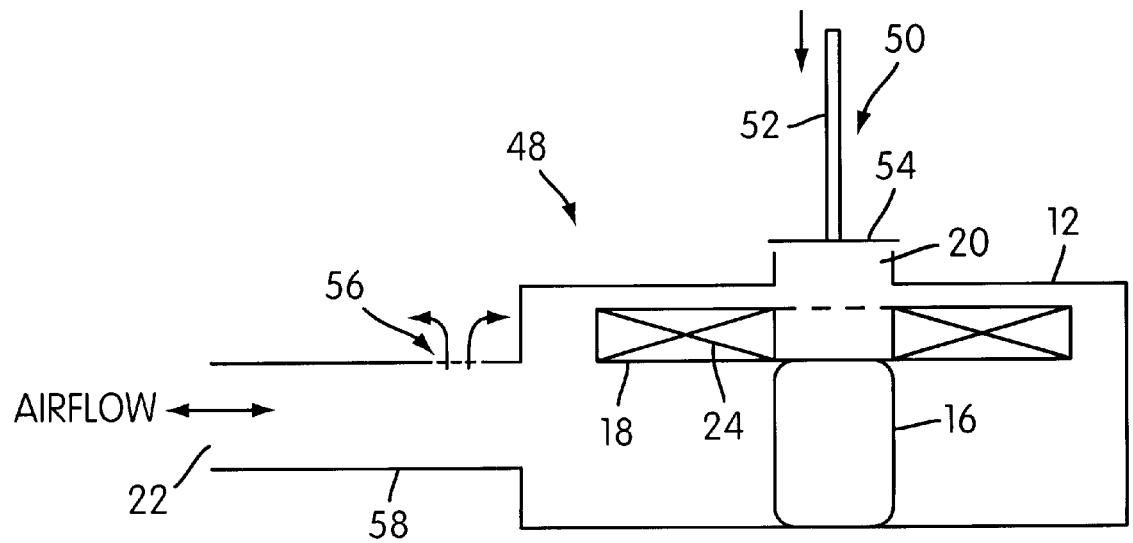

FIGS. 6 and 7 show another embodiment of a controllable flow generator 48, in which the supply of air or breathable gas to the inlet 20 is controllably restricted (and thus the flow generator efficiency reduced) by a choke 50 formed by a shaft 52 ending in a choke plate 54. Therefore, by the proximity of the plate 54 to the entrance to the air inlet 20, the air or breathable gas available to the turbine 18 can be controlled. As shown in FIG. 6, the choke plate is remote from the opening to the air inlet 20, hence there is no restriction of the flow of air or breathable gas into the inlet and to the turbine 18. This represents the situation of the maximum treatment pressure for a given operational rotational speed of the turbine 18. The situation shown in FIG.

7, where the choke plate 54 is seated against the mouth of the air inlet 20 to restrict any flow of air or breathable gas to the inlet, represents the lowest possible treatment pressure for the turbine 18 operating at or near the same operational rotational speed. Clearly, treatment pressures intermediate of the limits represented by the arrangements shown in FIGS. 6 and 7 are achieved by vertical movement of the choke shaft 52 to provide the necessary restriction of the entrance to the air inlet 20.

During the administration of bi-level CPAP treatment, the exhalation treatment pressure will be low, in which case the choke plate 54 will be almost seated on the mouth of the air inlet 20, which creates a high impedance path for patient expiration. For this reason, a bleed vent 56 is located in a tube 58 extending from the fan chamber 12 to the outlet 22. The bleed vent 56 provides a low impedance exhalation path for the patient. As will be apparent, the bleed vent 56 also represents a leak that will have a minor effect upon the pressure of air or breathable gas at the outlet 22 for the treatment pressures experienced during single level CPAP or during inspiration in bi-level CPAP treatment. The small pressure drop induced by the bleed vent 56 can easily be compensated by appropriate adjustment of the choke 50. The actuating circuit controlling the choke 50 may be operable under feedback control from a sensor sensing pressure at the mask of at the outlet 22, in which case the pressure drop due to bleed vent 56 will automatically be compensated. The bleed vent 56 should not incur a pressure drop in excess of 2 cm $H_2O$ otherwise minimum expiration treatment pressure might be compromised.

Figure 8:
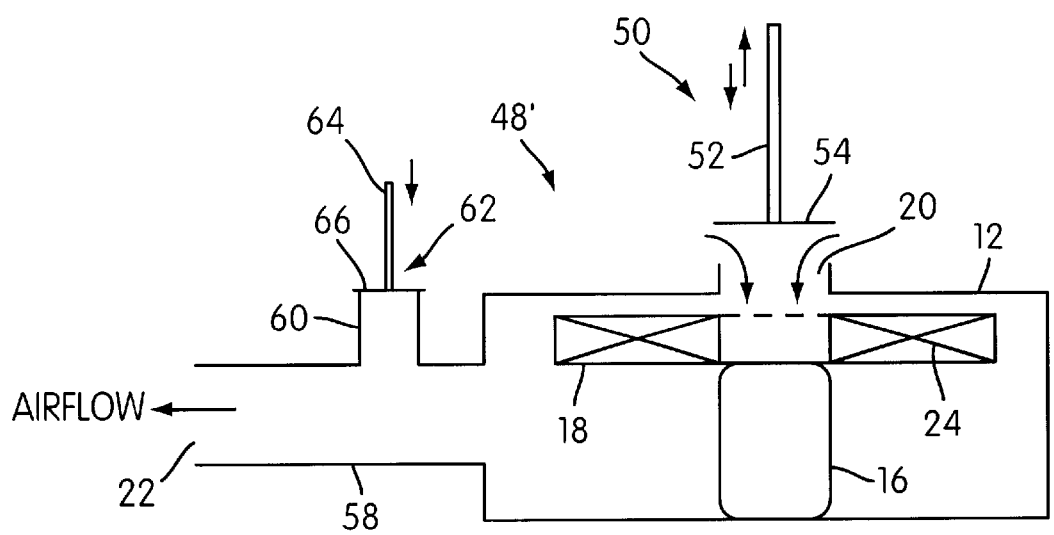
FIGS. 8 and 9 show a vet further embodiment of a controlled flow generator.
Figure 9:
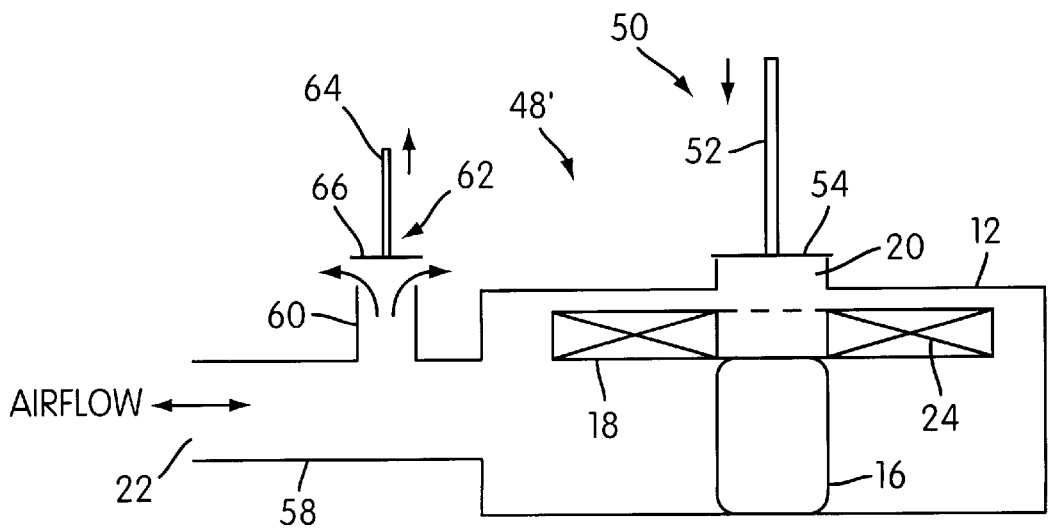

FIGS. 8 and 9 show a controllable flow generator 48' having an alternate arrangement for the bleed vent 56 of FIGS. 6 and 7, in that in certain instances it may not be desirable to have the bleed vent 56 open in any circumstances other than during patient expiration (e.g. bi-level CPAP treatment). As shown, the bleed vent 56 is replaced by a branch 60, and is in communication with the air outlet 22. The branch 60 is controllably opened and closed by a valve 62 formed by a valve shaft 64 and valve plate 66. The case of FIG. 8 relates to the provision of inspiratory treatment pressure in bi-level CPAP treatment, in which case the valve plate 66 closes-off the branch 60 so there is no leak from the outlet 22, and thus the full inspiratory output pressure from the flow generator 10 is delivered to the air delivery tube (not shown) and so to the mask (also not shown). The case of FIG. 9 relates to the provision of expiratory treatment pressure, whereby the choke plate 54 closes-off the mouth of the air inlet 22, and the branch 60, by actuation of the valve 62, is opened to the atmosphere to provide an exhalation path. Actuation of the choke 50 and the valve 62 can be synchronized, and it is preferable that there be a graduating opening of the mouth of the branch 60 in operation of the valve 62 rather than a sudden opening, to linearise the relationship between pressure and valve displacement. The arrangement of the branch 60 and the valve 62 must be such as to ensure that the pressure drop does not exceed the minimum expiration treatment pressure, typically 4 cm $H_2O$, and most preferably does not exceed 2 cm $H_2O$.

Figure 10:
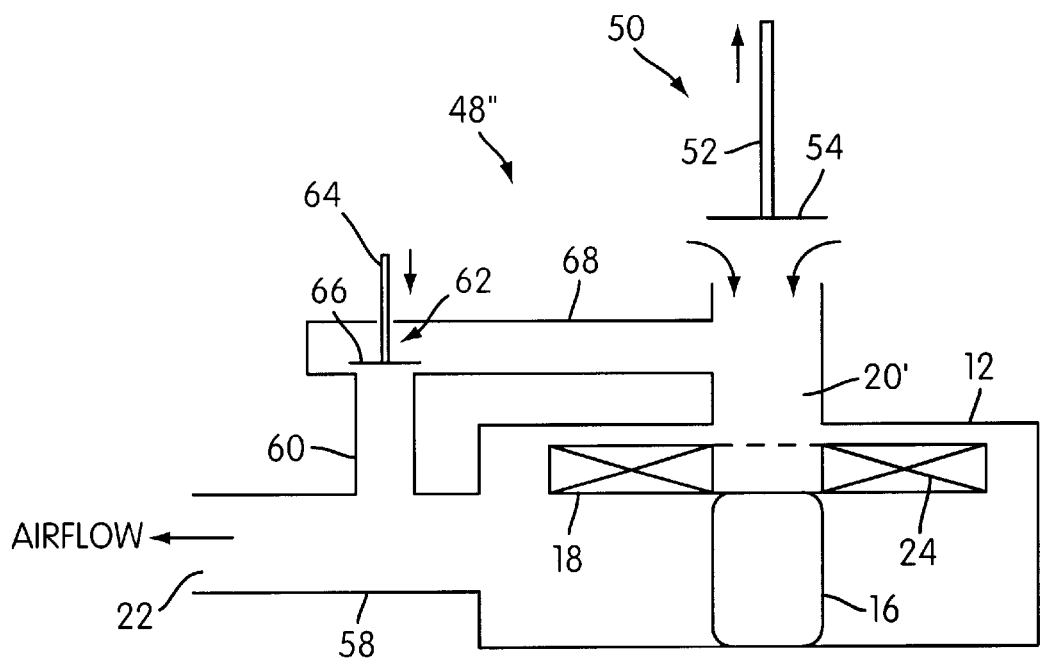
FIGS. 10 and 11 show a yet further embodiment of a controlled flow generator.
Figure 11:
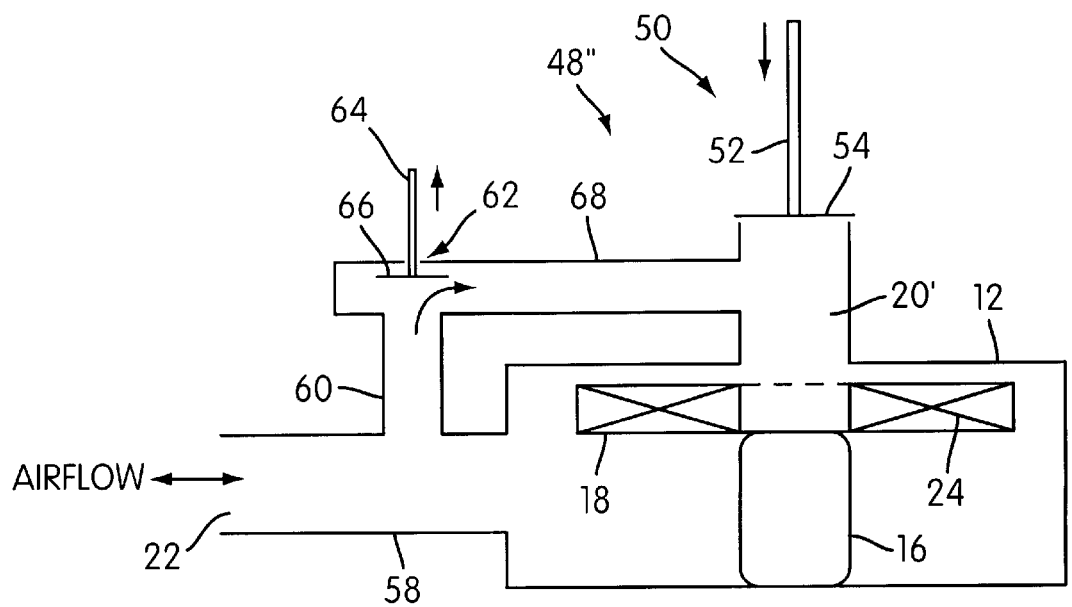

The arrangement shown in FIGS. 10 and 11 show a controllable flow generator 48" that is a variation of the embodiment of FIGS. 8 and 9, in that there is a recirculation conduit 68 connecting the branch 60 with the air inlet 20'. Thus air or breathable gas is recirculated during patient expiration, which avoids the necessity to vent to atmosphere, and thus removes a possible noise source. In FIG. 10, the valve plate 66 closes off the exit to the branch 60 during the provision of inspiration treatment pressure, with the valve 62 gradually being raised upwards at the transition to patient expiration to open the branch 60 to the recirculation conduit 68, as shown in FIG. 11, thus providing the recirculation path during patient expiration.

Figure 12A:
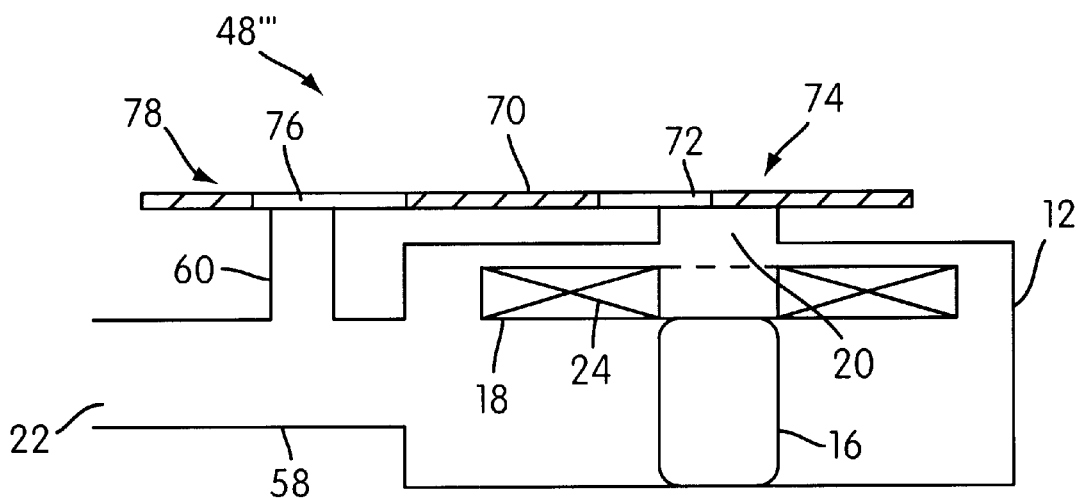
FIGS. 12a and 12b respectively show a cross-sectional and plan view of a further embodiment of a controlled flow generator.
Figure 12B:
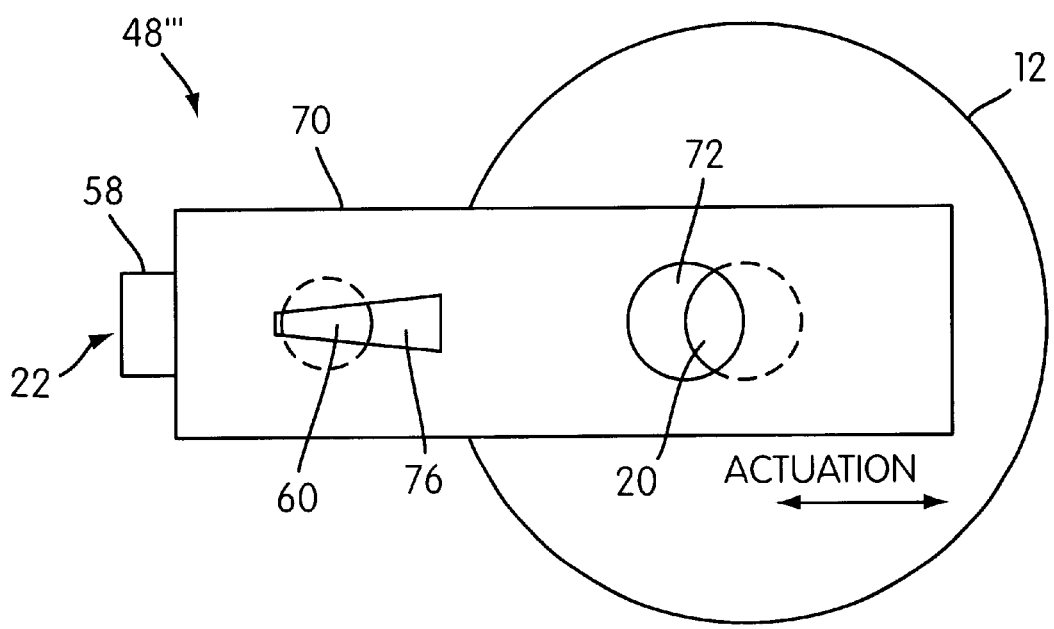

FIGS. 12a and 12b show a yet further embodiment of a controllable flow generator 48''' that is similar to the embodiments of FIGS. 8 and 9. In place of the choke 50 and valve 62 is a sliding pressure control plate 70. The pressure control plate 70 has a circular aperture 72 which in conjunction with the entrance to the air inlet 20 forms a choke valve 74. The aperture equally could be profiled in a non-regular shape. The plate 70 also has a profiled slot 76 which in conjunction with the exit to the branch 60 forms an impedance control valve 78.

The control plate 40 is slidingly operated by an actuator (not shown) having connection with the breathing detection and treatment pressure control circuitry. As the plate 70 moves to the left to further restrict the mouth of the inlet 20, the effective surface area at the exit of the branch 60 open through the slot 76 is commensurately increased, thus providing a lower impedance exhalation path. The converse situation applies when the plate 70 is moved to the right, in that when the circular aperture 72 is located wholly over the mouth of the inlet 20 corresponding to inspiration treatment pressure, the exit of the branch 70 is wholly blocked-off by the control plate 70, as the slot 76 will have past the left-most extent of the exit to the branch 60. The tapered arrangement for the slot 76 is one of many possible arrangements and, in this case, provides a near linear relation between exhalation impedance and treatment pressure.

Figure 13:
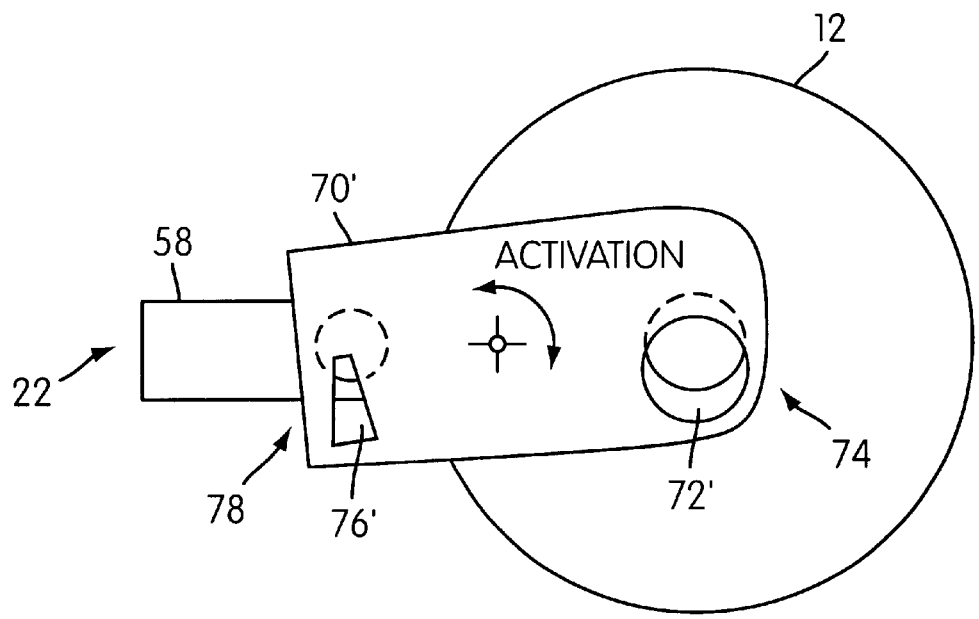
FIG. 13 shows a variation to the controlled flow generator shown in FIGS. 12a and 12b.

FIG. 13 shows an alternate arrangement to that of FIGS. 12a and 12b wherein the pressure control plate 70'' is no longer sliding, but rather rotatable, otherwise the principle of operation remains the same.

Figure 14:
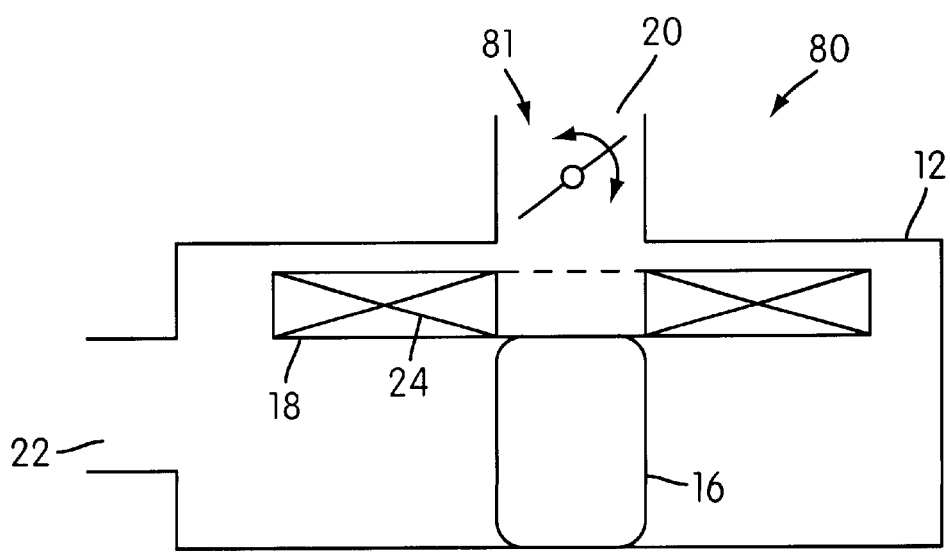
FIG. 14 shows a yet further embodiment of a controlled flow generator.

FIG. 14 shows a yet further embodiment of a controllable flow generator 80 that is somewhat similar to the arrangement shown in FIGS. 6 and 7. In this arrangement, the air available to the turbine 18 is controlled by a butterfly choke valve 81 that acts to restrict the air inlet 22 to the flow of air or breathable gas. Operation of this flow generator is otherwise as described in relation to FIGS. 6 and 7. Although not shown, as with FIGS. 6 and 7, a bleed vent can be provided downstream of the turbine 18 to provide a low impedance exhalation path.

The actuators that can be used in relation to all of the valve arrangements previously described can include linear or rotary arrangements of solenoids, brushless motors/actuators, stepper motors/actuators or switched reluctance motors/actuators.

Figure 15:
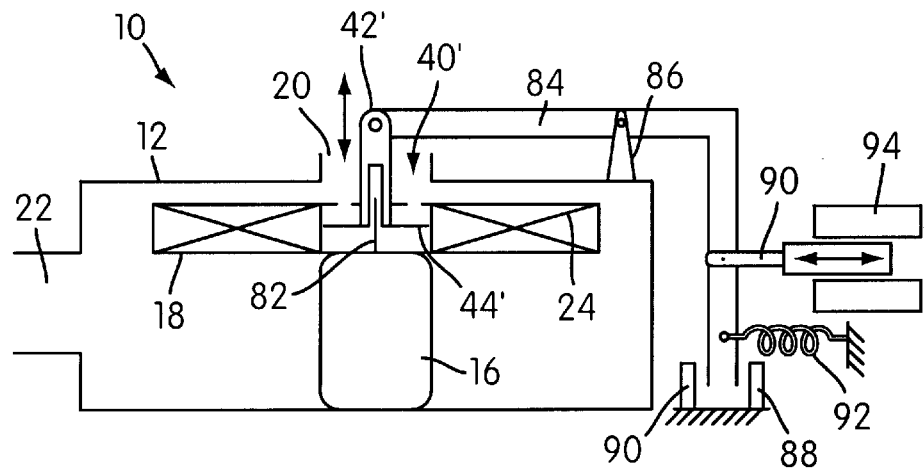
FIG. 15 shows an embodiment of a controlled flow generator including an arrangement for actuation.

One example of an actuator is shown in FIG. 15, which relates generally to the controllable flow generator shown in FIGS. 3–5. The baffle plate 44 is not in contact with the turbine blades 24 (or blade housing) hence is non-rotating, and is aligned by means of a locating pin 82. The shaft 42' is pivotably connected with an activating link 84, in turn pivotably mounted from a post 86 standing from the fan chamber 12. The activating link 84 is "L"-shaped, with the downwardly-directed leg having connection with an armature 90 and a helical spring 92. The armature 90 is under the control of a solenoid 94 that has connection at least with the breathing detection circuit. The spring 92 provides a return force when the solenoid is unpowered. Thus in response to the detection of transitions between inspiration and expiration, the solenoid 94 causes the armature 90 to move, in turn moving the activating link 94 and so the baffle plate 44 to control the desired treatment pressure between patient inspiration and expiration.

The solenoid 94 also can be connected to the pressure control circuitry to provide fine control over the desired treatment pressure, particularly and in the regulation of that pressure.

In another form, the solenoid 95 can be connected only to the breathing detection circuit, and for bi-level CPAP treatment the inspirating and expiratory treatment pressures can be mechanically selected by means of respective end stops 88, 90. For such an arrangement it is not necessary to retain the pressure control circuitry, which can lead to a cheaper product to put into the marketplace.

Figure 16:
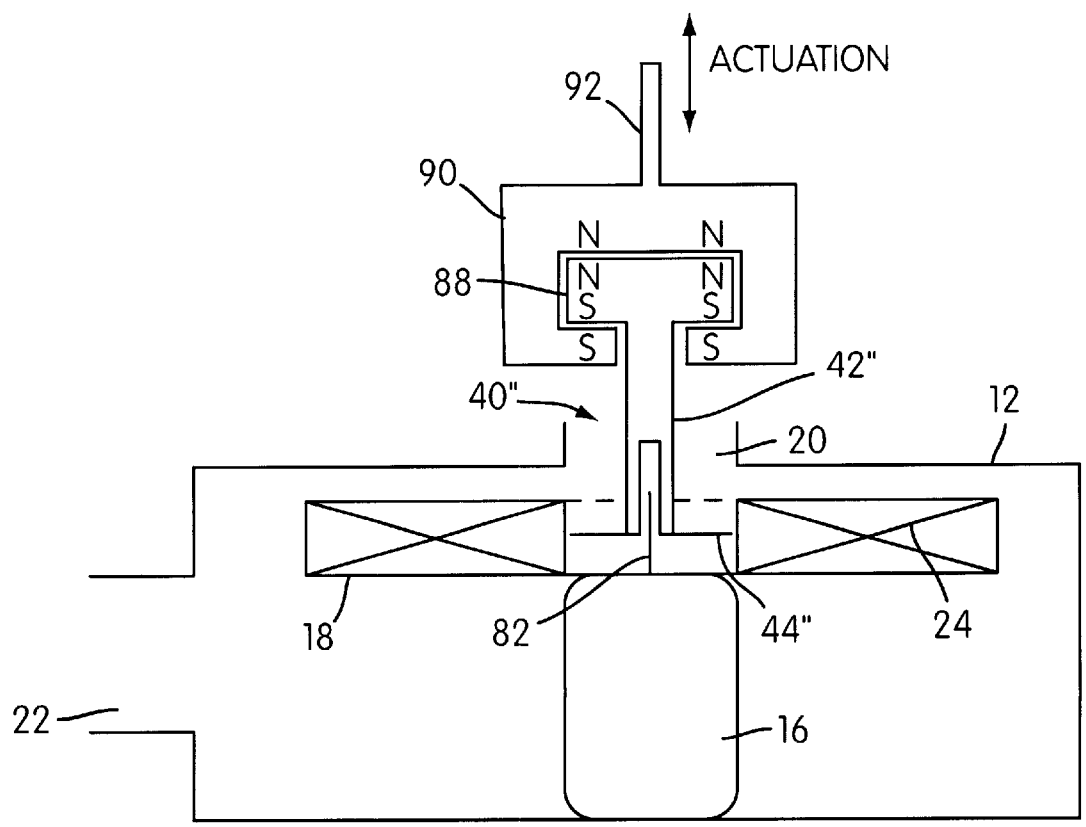
FIG. 16 shows an alternative arrangement for actuation of the controlled flow generator of FIG. 15.

FIG. 16 shows an alternative arrangement for an actuator for the controllable flow generator shown in FIG. 15. In this case, the baffle plate 44 can be in contact with the turbine blades 24 (or blade housing) so that the shaft 42" may rotate with the turbine 18. The upper end of the shaft 42" carries a permanent or electro-magnet 88 that is surrounded by a further permanent magnet 90 forming a magnetic link. In this way, the instance of the shaft 42" rotating in concert with the fan 18 can be accommodated, and actuation of the baffle plate 44" is by the vertical movement of the shaft 92 connected with the outer permanent or electromagnet assembly 90.

Figure 17:
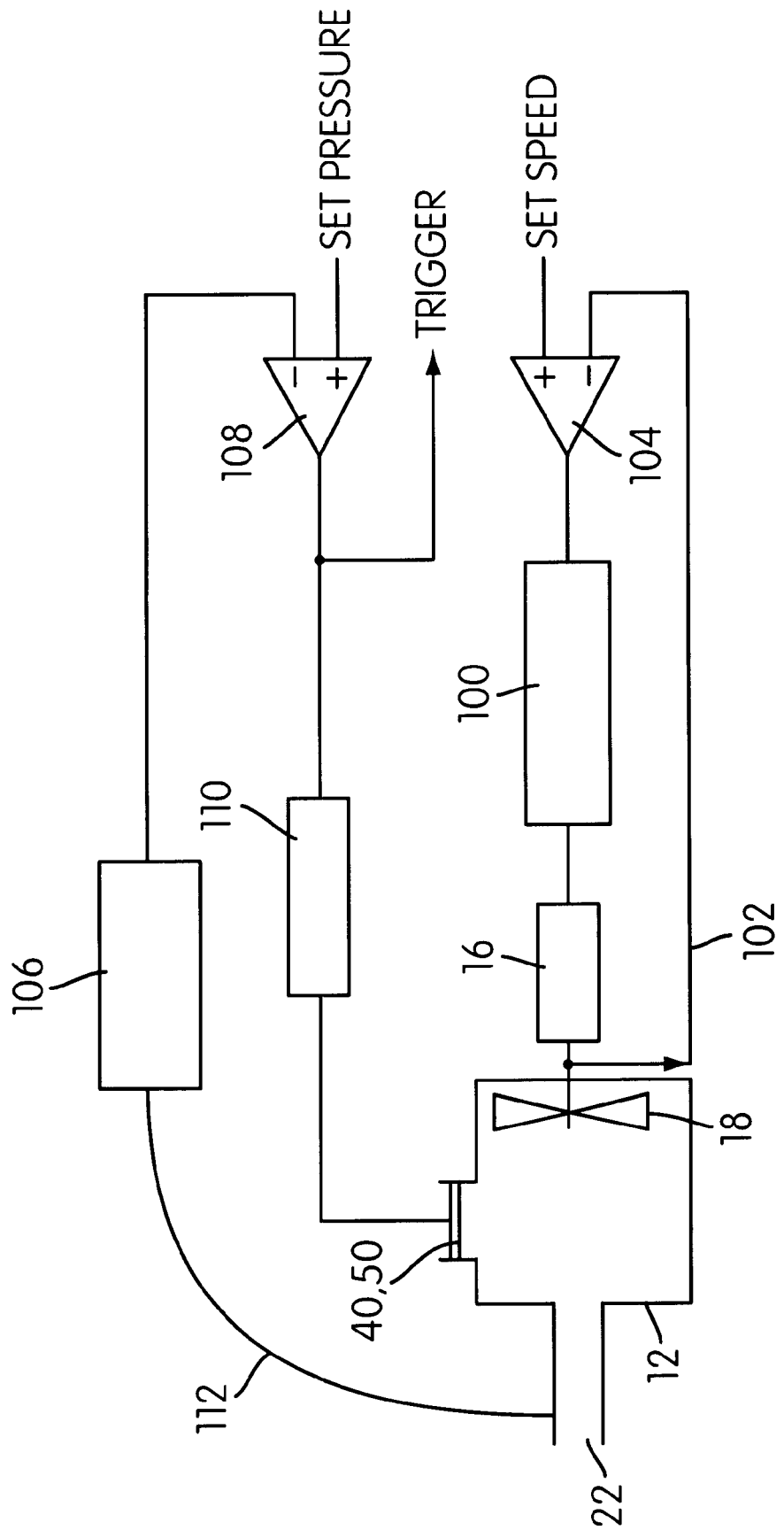
FIG. 17 is a schematic block diagram of CPAP apparatus including any one of the controllable flow generators of the preceding figures.

FIG. 17 shows a representative block diagram of control of CPAP apparatus incorporating controllable flow generator in accordance with any one of the preceding embodiments. The turbine 18 is driven at an operational rotational speed by the motor 16 under the control of a motor controller 100, with the rotational speed being held essentially constant at a "set speed", the regulation being provided by a comparison between the "set speed" signal and a feedback signal 102 by a comparator 104. It is of course possible for the "set speed" signal to vary, although treatment pressure control is not effected by motor speed control. In that case, the "set pressure" signal is independent of the "set speeds" signal, and is compared with the output of a pressure transducer 106 that measures pressure at the flow generator outlet 22 (via tube 112) by a comparator 108. The sensed pressure can alternatively be the treatment pressure at the mask. The error signal between the set pressure and the measured pressure at the outlet 22 causes the actuator 110 to adjust the position of the control element/choke 40, 50. The "set pressure" signal can be constant for single level CPAP, or can vary in the instance of bi-level CPAP or autosetting CPAP treatment.

The output signal from the pressure comparator 108 will reflect respiration rate and depth, and so also can be used as a signal to trigger transitions between patient inspiration and expiration. This may lead to a simplification or even redundancy of existing breathing detection circuitry. It also provides a measure of flow, minute volume and like parameters.

FIGS. 18a, 18b, 19a and 19b show two arrangements in which the efficiency of a flow generator is controlled by way of the pneumatic impedance of the outlet of the flow generator available to the exiting breathable gas. The impedance of the flow generator is effected in the sense that a change in cross-sectional area or volumetric capacity of the outlet will effect the ability to pressurize a mass of air at a given flow rate and given pressure, as will be apparent to one skilled in the art.

Figure 18A:
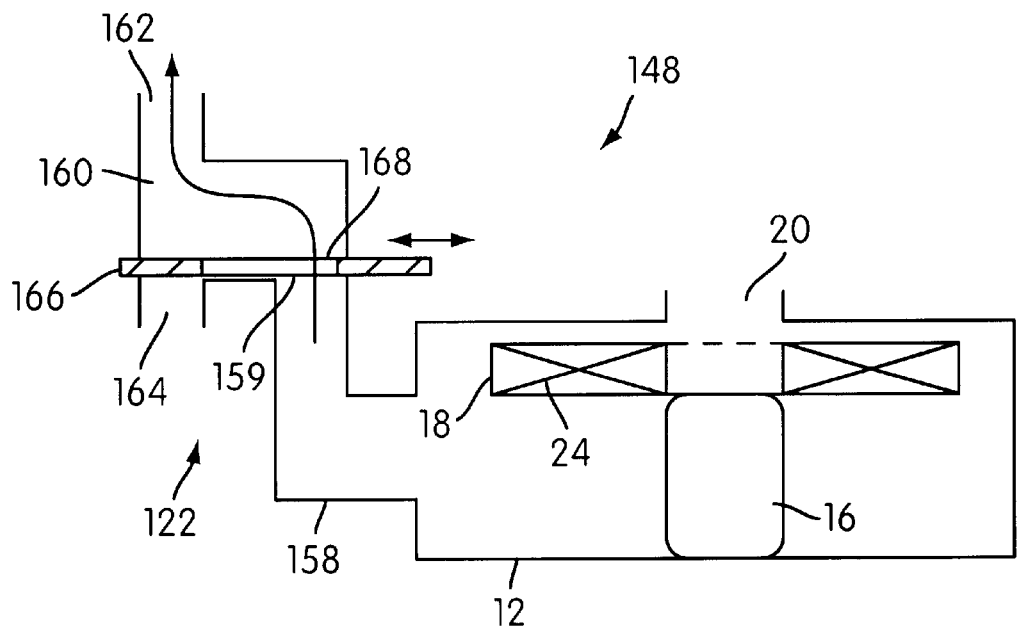
FIGS. 18a and 18b show a cross-sectional view of a further embodiment of a controlled flow generator.
Figure 18B:
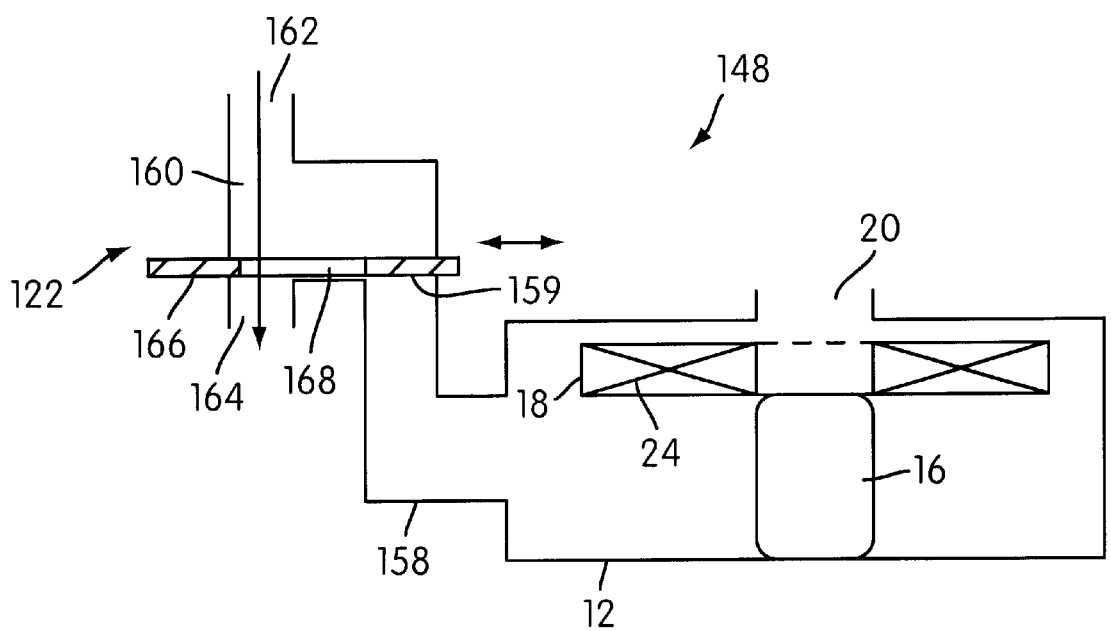

The flow generator 148 shown in FIGS. 18a and 18b includes a number of elements common with the embodiments previously described. A passageway 158 exits from the chamber 12 and communicates the exiting gas with a plenum 160 via an entrance 159. The plenum has an exiting port 162, by which pressurised breathable gas can be supplied via a conduit to a patient mask for the administration of CPAP treatment or assisted respiration. The plenum 160 has a further vent 164 in communication with atmosphere. Both the vent 164 and the entrance 159 to the plenum 160 can be controllably occluded to reduce their open area by a sliding impedance control plate 166. The control plate 166 includes an aperture 168 that, depending upon its position, can restrict the respective passages in a range from wholly open to fully closed.

In FIG. 18a, the control plate 166 is in a position such that the aperture 168 occludes the control vent 164 yet allows communication of exiting breathable gas from the passageway 158 to the plenum 160 and so to the exiting port 162. The direction of flow of breathable gas is shown by the line bearing an arrowhead. FIG. 18b shows the situation where the control plate 166 is in a position whereby the entrance 159 is closed, however the impedance control vent 164 is open. This condition accords with the provision of a low impedance path for patient expiration.

Clearly FIGS. 18a and 18b show the extreme ranges of operation of the impedance control plate 166. The aperture 168 is sized so that the entrance 159 to the plenum 160 can be partially open, as can the control vent 164. In this manner, the impedance of the outlet 122 is controllable, in turn, controlling the efficiency of the flow generator 148.

Figure 19A:
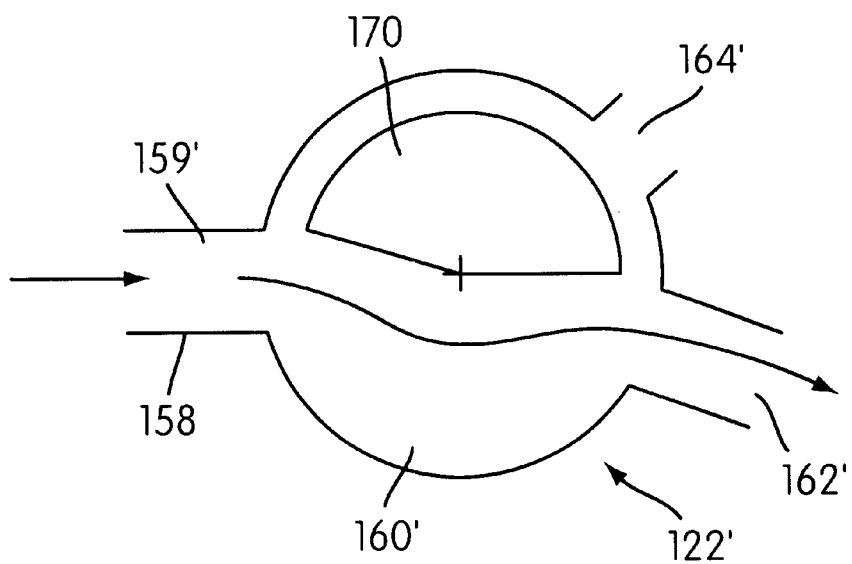
FIGS. 19a and 19b show a schematic view of a yet further embodiment of a controlled flow generator.
Figure 19B:
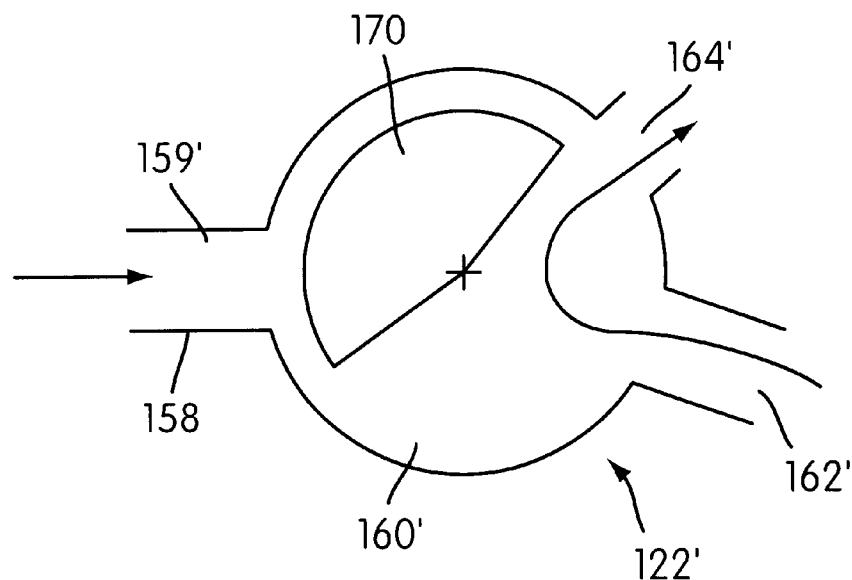

FIGS. 19a and 19b show a further embodiment of an outlet section 122' as an alternative arrangement to the outlet section 122 shown in FIGS. 18a and 18b. Again, common elements have been indicated by use of like reference numerals. The plenum 160' is of circular cross-section. In place of the previous sliding impedance control plate 166 is a rotatable control plate 170. In the position shown in FIG. 19a, the vent 164' is occluded by the control plate 170, meaning that the full flow of gas from the turbine passes from the passageway 158 through the plenum 160' to the exiting opening 162'. This situation represents the maximum treatment pressure.

The situation shown in FIG. 19b is where the impedance control plate 170 now fully occludes the entrance 159' to the plenum 160' resulting in the minimum output pressure, again, providing a low impedance path on patient expiration.

For both of the embodiments of FIGS. 18a, 18b, 19a and 19b, the arrangements for controlling the respective impedance control plates previously applied 166, 170 equally apply.

In another embodiment not specifically shown in the drawings, the turbine can have adjustable pitch or sized impeller blades that are controllable to effect a change in the turbine, and hence flow generator efficiency, and in this way have control over output pressure. Such turbines also may have louvre arrangements to spoil air flow and adjust efficiency.

Figure 20A:
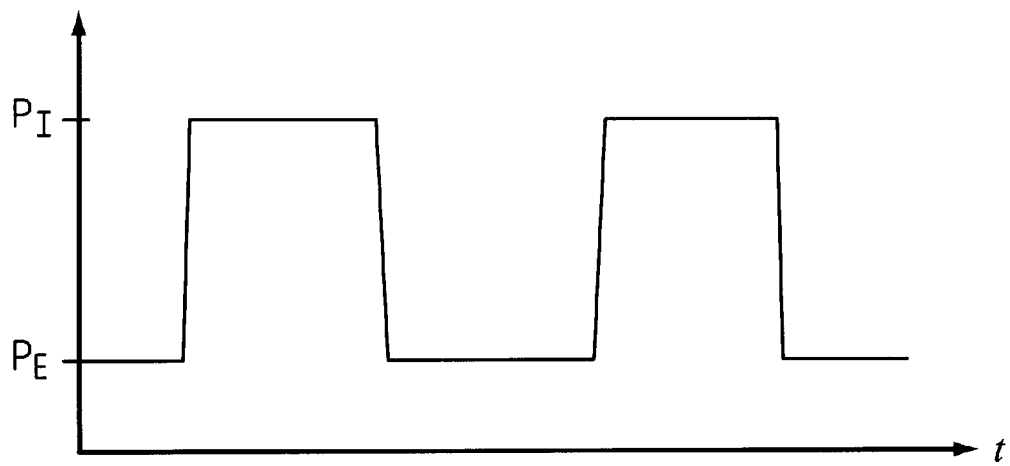
FIGS. 20a–20d show examples of pressure transition functions.
Figure 20B:
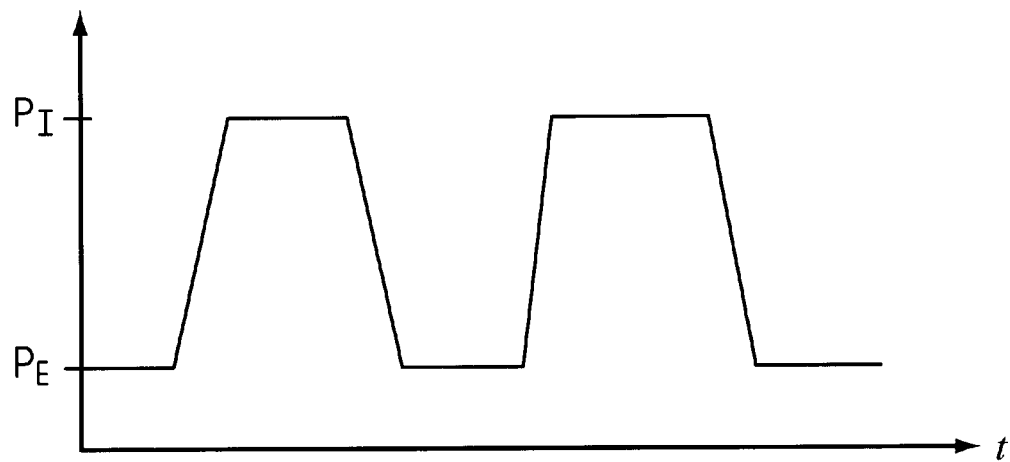
Figure 20C:
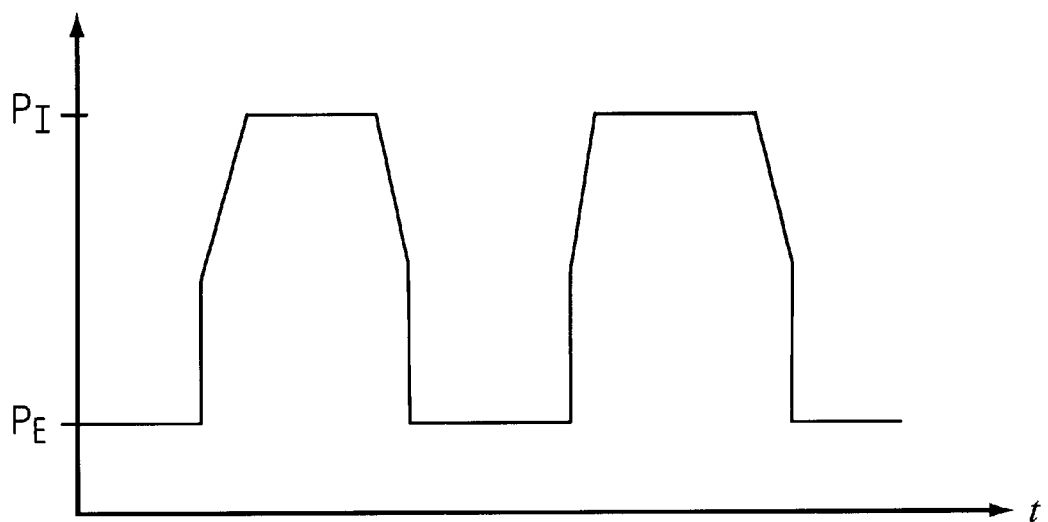
Figure 20D:
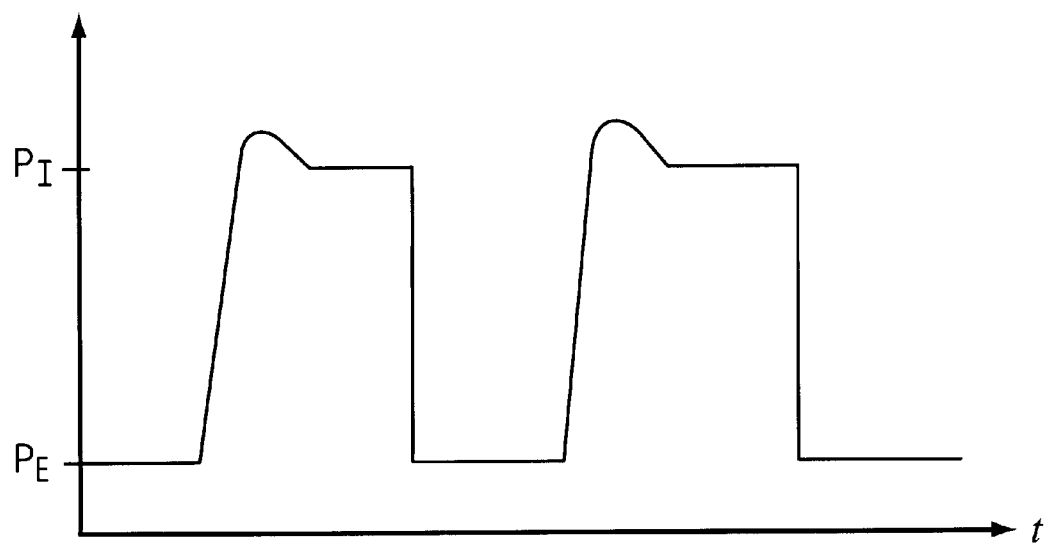

In all the valve/choke arrangements previously described a number of bi-level CPAP inspiration/expiration transitional schemes can be adopted. A first case, as shown in FIG. 20a an impulsive chance between treatment pressure that is a fast rising pressure output, having a rate of rise of approximately 0.5-1.0 cm $H_2O$ per msec. A second case, as shown in FIG. 20b is a linear ramping function, having a gradient typically between 0.2-0.04 cm $H_2O$ per msec. The third case, as shown in FIG. 20c is a combination of the first two, as an impulsive step followed by a ramp. The step may be of the order ½ ($P_I$–$P_E$) Finally, FIG. 20d shows a case where the rising ramp has an overpressure (>$P_I$) at the commencement of the inspiratory phase, and an impulsive change the transition to the inspiratory phase.

Figure 21:
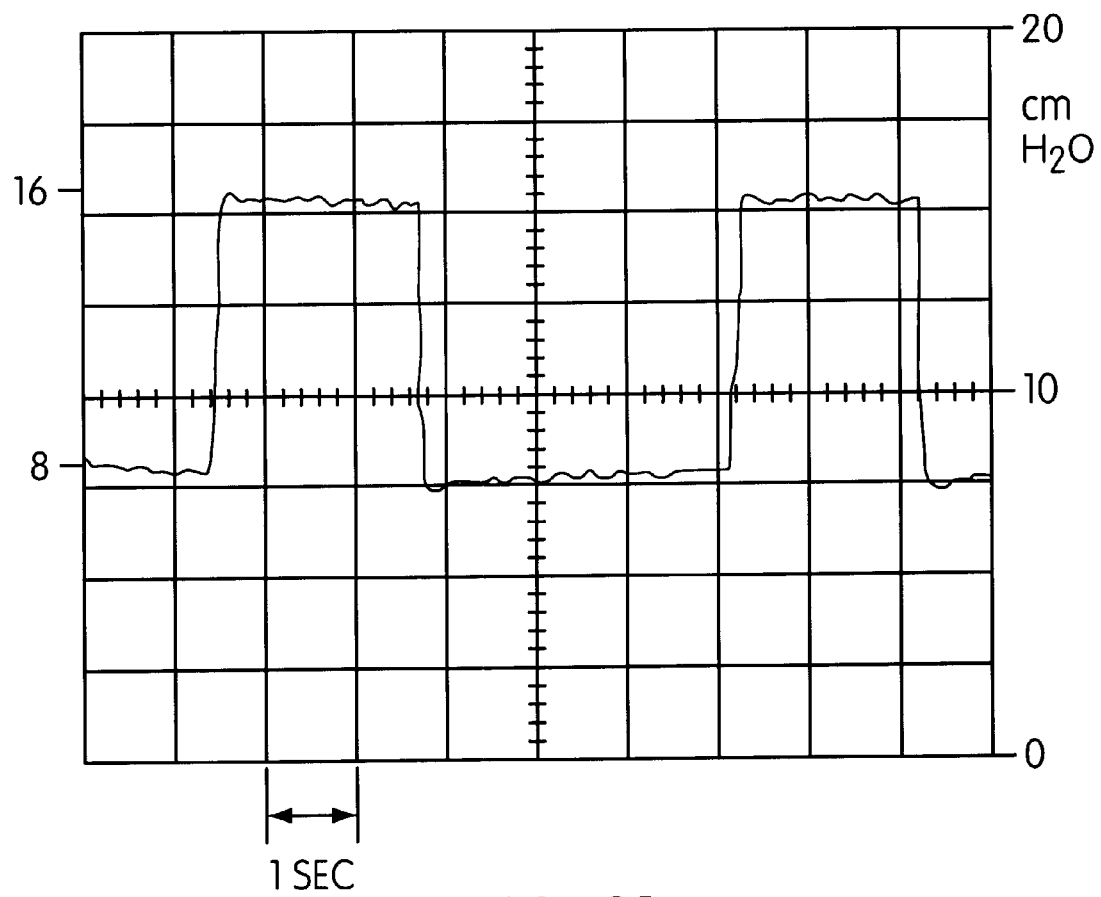
FIG. 21 shows a graph of pressure versus time for the flow generator of FIGS. 12a and 12b.

FIG. 21 shows a chart of measured outlet pressure versus time for bi-level operation of the embodiment described in FIGS. 12 and 12b, for which the inspiratory treatment pressure is about 16 cm $H_2O$ and the expiratory treatment pressure is about 8 cm $H_2O$.

While the embodiments described have the turbine operating at a constant rotational speed, it is equally possible to combine motor speed control with flow generator efficiency (e.g. control over the air or breathable gas available to the turbine) in the course of control over output pressure.

What is claimed is:

1. A controllable flow generator for supplying breathable pressurized gas, the flow generator comprising:

a housing with an inlet to receive the gas;

a blower within the housing in communication with the inlet;

a motor coupled to drive the blower, thereby pressurizing and providing the received gas to a passageway in communication with the housing; and a valving system in communication with the passageway, the valving system including a movable control member within the valving system, an entrance in communication with the passageway, an exiting port, and a vent positioned between the entrance and the exiting port in controlled gas communication with atmosphere, wherein in an inspiratory mode of operation, the movable control member is movable to increase an open area of the entrance while decreasing the open area of the vent, thereby controllably directing the gas introduced into the valving system via the entrance to a desired degree to the exiting port, and in an expiratory mode of operation, the movable control member is movable to increase the open area of the vent while decreasing the open area of the entrance, thereby controllably directing gas introduced into the valving system via the entrance and gas introduced into the valving system via the exiting port to a desired degree to the vent.

2. The flow generator of claim 1, wherein the movable control member is pivotable.

3. A valving system comprising:

an entrance, an exiting port, and a vent positioned between the entrance and the exiting port in controlled gas communication with atmosphere; and a movable control member in communication with the entrance, exiting port and vent, wherein in an inspiratory mode of operation, the movable control member is movable to increase an open area of the entrance while decreasing the open area of the vent, thereby controllably directing the gas introduced into the valving system via the entrance to a desired degree to the exiting port, and in an expiratory mode of operation, the movable control member is movable to increase the open area of the vent while decreasing the open area of the entrance, thereby controllably directing gas introduced into the valving system via the entrance and gas introduced into the valving system via the exiting port to a desired degree to the vent.

4. The valving system of claim 3, wherein the movable control member is pivotable.

* * * * *

UNITED STATES PATENT AND TRADEMARK OFFICE
CERTIFICATE OF CORRECTION

PATENT NO.     : 6,526,974 B1
DATED          : March 4, 2003
INVENTOR(S)    : Brydon et al.

It is certified that error appears in the above-identified patent and that said Letters Patent is hereby corrected as shown below:

Title page,
Item [63], Related U.S. Application Data, should read
-- [63] Continuation of application No. 08/894,305, filed as application No. PCT/AU96/00586 on Sep. 18, 1996, now Pat No. 6,182,657. --

Item [30], Foreign Application Priority Data, should read
-- Sep. 18, 1995 (AU) .........PN5498
Dec. 28, 1995   (AU) .........PN7359
May 9, 1996     (AU) .........PN9761 --

Signed and Sealed this

Twenty-third Day of December, 2003

JAMES E. ROGAN
*Director of the United States Patent and Trademark Office*